United States Patent
Naidoo et al.

(10) Patent No.: US 10,009,577 B2
(45) Date of Patent: Jun. 26, 2018

(54) COMMUNICATION SYSTEMS

(75) Inventors: Surendra N. Naidoo, Austin, TX (US); Michael G. McCown, Austin, TX (US)

(73) Assignee: Comcast Cable Communications, LLC, Philadelphia, PA (US)

( * ) Notice: Subject to any disclaimer, the term of this patent is extended or adjusted under 35 U.S.C. 154(b) by 711 days.

(21) Appl. No.: 13/618,919

(22) Filed: Sep. 14, 2012

(65) Prior Publication Data
US 2013/0070044 A1 Mar. 21, 2013

Related U.S. Application Data

(63) Continuation of application No. 10/230,834, filed on Aug. 29, 2002, now abandoned.

(51) Int. Cl.
| | | |
|---|---|---|
| *H04N 7/14* | (2006.01) | |
| *H04W 4/06* | (2009.01) | |
| *G06F 19/00* | (2018.01) | |
| *G06Q 50/22* | (2018.01) | |
| *G06Q 10/10* | (2012.01) | |

(Continued)

(52) U.S. Cl.
CPC .......... *H04N 7/14* (2013.01); *G06F 19/3418* (2013.01); *G06Q 10/10* (2013.01); *G06Q 50/22* (2013.01); *H04W 4/06* (2013.01); *H04W 4/90* (2018.02); *A61B 5/0022* (2013.01); *A61B 5/747* (2013.01); *H04L 67/12* (2013.01); *H04L 67/26* (2013.01); *H04M 3/5116* (2013.01); *H04M 2201/50* (2013.01); *H04M 2242/04* (2013.01); *H04N 7/147* (2013.01); *H04N 21/4788* (2013.01); *H04N 21/4882* (2013.01)

(58) Field of Classification Search
None
See application file for complete search history.

(56) References Cited

U.S. PATENT DOCUMENTS

| | | | |
|---|---|---|---|
| 5,434,611 A | | 7/1995 | Tamura |
| 5,544,649 A | * | 8/1996 | David et al. .................. 600/301 |

(Continued)

FOREIGN PATENT DOCUMENTS

EP        1306793        5/2003

OTHER PUBLICATIONS

Harless WG, Zier Ma, Duncan RC, A voice-activated, interactive videodisc case study for use in the medical school classroom, J. Med. Educ. Nov. 1986; 61(11): 913-5.

(Continued)

*Primary Examiner* — Michael R Telan
(74) *Attorney, Agent, or Firm* — Baker & Hostetler LLP

(57) ABSTRACT

An integrated home health system includes a television-based patient station, a first provider station for providing telemedicine or other healthcare services to a patient located at the patient station, a second provider station for providing caregiver services to the patient, a third provider station for providing emergency response services to the patient and a system management station coupled together by a data network. In addition to various management operations performed on behalf of the integrated home health system, the system management station is further configured to provide various home health services to the patient located at the patient station, either alone, or in conjunction with one or more of the first, second and/or third provider stations.

33 Claims, 10 Drawing Sheets

(51) Int. Cl.
*H04L 29/08* (2006.01)
*H04N 21/4788* (2011.01)
*H04N 21/488* (2011.01)
*H04M 3/51* (2006.01)
*H04W 4/90* (2018.01)
*A61B 5/00* (2006.01)

(56) References Cited

U.S. PATENT DOCUMENTS

| | | |
|---|---|---|
| 5,553,609 A | 9/1996 | Chen et al. |
| 5,585,858 A | 12/1996 | Harper et al. |
| 5,596,994 A | 1/1997 | Bro |
| 5,601,435 A | 2/1997 | Quy |
| 5,666,293 A | 9/1997 | Metz et al. |
| 5,722,418 A | 3/1998 | Bro |
| 5,828,403 A | 10/1998 | DeRodeff et al. |
| 5,867,821 A | 2/1999 | Ballantyne et al. |
| 5,903,211 A | 5/1999 | Flego et al. |
| 5,961,446 A | 10/1999 | Beller et al. |
| 5,977,962 A | 11/1999 | Chapman et al. |
| 5,987,519 A * | 11/1999 | Peifer et al. ............ 709/230 |
| 5,997,476 A | 12/1999 | Brown |
| 6,032,119 A | 2/2000 | Brown et al. |
| 6,108,685 A | 8/2000 | Kutzik et al. |
| 6,144,837 A | 11/2000 | Quy |
| 6,166,730 A | 12/2000 | Goode et al. |
| 6,234,964 B1 | 5/2001 | Iliff |
| 6,246,992 B1 | 6/2001 | Brown |
| 6,334,778 B1 | 1/2002 | Brown |
| 6,339,842 B1 * | 1/2002 | Fernandez et al. .......... 725/133 |
| 6,375,469 B1 | 4/2002 | Brown |
| 6,381,577 B1 | 4/2002 | Brown |
| 6,408,330 B1 | 6/2002 | DeLaHuerga |
| 6,443,890 B1 | 9/2002 | Schulze et al. |
| 6,454,705 B1 | 9/2002 | Cosentino et al. |
| 6,463,417 B1 | 10/2002 | Schoenberg |
| 6,539,407 B1 | 3/2003 | Perlman et al. |
| 6,638,218 B2 | 10/2003 | Bulat |
| 6,757,358 B1 * | 6/2004 | Kondziela ............... 379/38 |
| 6,816,603 B2 | 11/2004 | David et al. |
| 6,916,291 B2 | 7/2005 | Givens et al. |
| 7,096,037 B2 * | 8/2006 | Canova et al. ........... 455/556.1 |
| 7,185,282 B1 | 2/2007 | Naidoo et al. |
| 7,835,926 B1 | 11/2010 | Naidoo et al. |
| 2003/0014762 A1 | 1/2003 | Conover et al. |
| 2003/0023459 A1 | 1/2003 | Shipon |
| 2003/0041333 A1* | 2/2003 | Allen ............ H04N 5/76 725/106 |
| 2003/0069002 A1 | 4/2003 | Hunter et al. |
| 2003/0069752 A1 | 4/2003 | LeDain et al. |
| 2004/0210824 A1 | 10/2004 | Shoff et al. |

OTHER PUBLICATIONS

"Philips Telemedicine Solutions: Extending the reach of remote patient management," available at http:www.medical.philips.com/main/products/telemonitoring/, printed on Jun. 1, 2007, 2 pgs.

"Motiva Interactive Healthcare Platform: Remote patient management and personalized education delivered through a patient's home television," and Motiva Fact Sheet available at http:www.medical.philips.com/main/products/telemonitoring/products/motiva-/index.html, printed on Jun. 1, 2007, 4 pgs.

"Philips announces U.S. commercial launch of Motiva—a TV-based platform of remote patient management," Philips Press Information, May 8, 2008, 3 pgs.

"Frost & Sullivan presents Philips with 2005 Technology Leadership Award: Philips excellence in European remote patient monitoring markets recognized," Frost & Sullivan Press Release, Dec. 12, 2005, 3 pgs.

"Adding automated daily home monitoring to telephone based disease management significantly reduced heart failure hospitalizations," Philips Press Information, Nov. 15, 2005, 2 pgs.

"Philips and Achmea to Launch First European Pilot Study of TV-Based System for Patients to Manage Health at Home," Achmea Press Information, Jun. 8, 2005, 3 pgs.

"U.S. Study Shows Chronic Disease Patients Embrace Philips Personalized TV-Based Interactive Healthcare Platform to Manage Disease From Home," Philips Press Information, Jun. 8, 2005, 3 pgs.

"Philips to Begin Pilot Study of TV-Based Solution to Help Patients Manage Their Health From Home," Philips Press Information, Oct. 15, 2004, 3 pgs.

"DMPC Cites Five Best DM Ideas of 2004," Disease Management News, vol. 10, No. 2, Jan. 25, 2005, 2 pgs.

"Ten-HMS Study Demonstrates Clinical and Financial Efficacy of Home Telemonitoring," Philips Telemonitoring Services, Sep. 2003, 4 pgs.

"Telemedicine: The Healthcare Environment Presents Many Challanges. Emblaze-VCON Collaboration Systems Are Specifically Designed for the Unique Requirements of HealthCare," available at http:www.vcon.com/solutions/telemedicine/, printed on Jun. 1, 2007, 1 pg.

"HD3000 / HD3000 LT: HD Set-Top Videoconferencing System," available at http:www.vcon.com/products/endpoints/group.videoconferencing.systems/HD30-00/index.shtml, printed on Jun. 1, 2007, 3 pgs.

"HD3000 High Quality Set-Top Videoconferencing System," Emblaze-VCON HD3000 Datasheet, Nov. 2006, 2 pgs.

Lee, Ren-Guey, et al., "Home Telecare System Using Cable Television Plants—An Experimental Field Trial," IEEE Transactions on Information Technology in Biomedicine, vol. 4, No. 1, Mar. 2000, pp. 37-44 (8 pgs.).

* cited by examiner

COMMUNICATION SYSTEMS

CROSS-REFERENCE TO RELATED APPLICATIONS

This application is a continuation of U.S. patent application Ser. No. 10/230,834 filed Aug. 29, 2002, now abandoned which relates to U.S. patent application Ser. No. 10/230,833 entitled "Method for Conducting a Home Health Session Using an Integrated Television-Based Broadband Home Health System," which issued as U.S. Pat. No. 7,835,926, and U.S. patent application Ser. No. 10/230,521 entitled "Interface Device for an Integrated Television-Based Broadband Home Health System," which issued as U.S. Pat. No. 7,185,282, each of which is hereby incorporated by reference in their entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present disclosure relates generally to communication systems and, more particularly, to a communication system which integrates one or more services.

BACKGROUND OF THE INVENTION

In an aspect, approximately 100 million Americans have a chronic condition such as heart disease, cancer, AIDS or diabetes. Of these, approximately 8 million receive at least one home care visit per year while approximately 3 million require 50 home care visits per year. Additionally, many people, particularly, the elderly, medically-at-risk and physically challenged, subscribe to personal emergency response services ("emergency response") to ensure quick and easy access to emergency help whenever needed. Currently, the cost of home healthcare and emergency response services is about 43 billion dollars. As the baby boomer generation continues to age, the number of people in need of home healthcare and/or emergency response services is expected to grow. For example, recent projections have estimated that the home healthcare and emergency response market will grow to over 64 billion dollars by 2006.

The extent to which remote healthcare delivery systems have been implemented varies widely depending on the particular type of remote healthcare delivery system involved. Some remote healthcare delivery systems, for example, remote caregiving systems, have rarely, if ever, been implemented. Other remote healthcare delivery systems, for example, telemedicine, have been widely implemented. Telemedicine is the use of electronic communication and information technologies to provide healthcare when distance separates the medical professional from the patient. A related type of remote healthcare delivery system is commonly known as "telehealth." Telehealth is the electronic provision of health care and information services for the direct benefit of individual patients and their families. It includes both actual physician-patient interactions via telemedicine, as well as education and information services designed to increase awareness of (and where applicable, compliance with) diagnoses and medical conditions, treatments, and good health practices. While the two terms are often used interchangeably, the underlying concept of telemedicine has traditionally described the use of technology to provide clinical medical services when the healthcare provider and patient are separated by geographic distance. Telehealth, on the other hand, should be viewed as an expansion on telemedicine. More specifically, telehealth not only includes clinical services but also non-clinical medical services such as education, research, and administrative functions.

It should be readily appreciated that the wellness and peace of mind of many individuals and their families would benefit greatly from a home health system that provides various ones of the emergency response, life safety, telemedicine, telehealth and remote caregiving services in a single, integrated, home health system. It should be further appreciated that access to integrated home health systems would be enhanced if such systems were configured to exploit the existing cable broadband infrastructure. It is, therefore, the object of this invention to provide an integrated home health system capable of achieving various ones of the aforementioned benefits.

SUMMARY OF THE INVENTION

In one embodiment, the present invention is directed to an integrated home health system which includes a patient station, a broadband access device coupled to the patient station, a data network coupled to the broadband access device and a home health services provider station coupled to the data network. The home health services provider station provides home health services to the patient station over a broadband connection with the data network provided by the broadband access device. In one aspect thereof, the patient station includes an interface device, coupled to the broadband access device, which enables two-way video and audio exchanges between the home health services provider station and the patient station. In another, the patient station further includes a television set coupled to the interface device. In this aspect, video and audio signals received from the home health services provider station are transmitted, by the interface device, to the television set for broadcast thereby.

In other aspects of this embodiment of the invention, the patient station may further include a digital imager and an audio receiver respectively coupled to the interface device. In these aspects, the interface device transmits video and audio signals received from the digital imager and the audio receiver, respectively, to the home health services provider station. In still others, the patient station may also include a medical device coupled to the interface device. In these aspects, the interface device transmits data signals received from the medical device to the home health services provider station.

In still other aspects of this embodiment of the invention, the integrated home health system may further include a system management station, coupled to the data network, for authorizing the home health provider station to provide home health services to the patient station and/or provide additional home health services to the patient station over the broadband connection with the data network provided by the broadband access device. In certain ones of these aspects, the interface device would transmit data signals, received from the medical device, to both the home health services provider station and the system management station. In further aspects thereof, the integrated home health system may further include an emergency response station coupled to the data network and the public switched telephone network ("PSTN") while the patient station further includes an emergency response device coupled to the interface device and the PSTN. In this aspect, the emergency response device is configured for two-way audio exchanges with the emergency response station along a first path which passes through the PSTN and along a second path which passes through the interface device, the broadband access device and the data network. In other aspects thereof, upon receiving, from the emergency response device, a request for connection to the emergency response station, the interface device determines whether the requested connection should be established using the first path or the second path.

In another embodiment, the present invention is directed to an integrated home health system which includes a patient station, a remotely located health care provider station and a remotely located caregiver provider station coupled to one another by a data network. In one aspect thereof, the integrated home health system further includes a broadband access device which couples the patient station to the data network. In another, the patient station includes an interface device, coupled to the broadband access device, for enabling two-way video and audio exchanges between the healthcare provider station and the patient station during healthcare sessions and two-way video and audio exchanges between the caregiver provider station and the patient station during caregiver sessions. In still another, the patient station further includes a television set coupled to the interface device. In this aspect, the interface device transmits video and audio signals, received from the healthcare provider station during the healthcare sessions and from the caregiver provider station during the caregiver sessions, to the television set for broadcast thereby.

In other aspects of this embodiment of the invention, the patient station may further include a digital imager and an audio receiver respectively coupled to the interface device. In these aspects, the interface device transmits video and audio signals received from the digital imager and the audio receiver, respectively, to the healthcare provider station during the healthcare sessions and to the caregiver provider station during the caregiver sessions. In still others, the patient station may also include a medical device coupled to the interface device. The interface device may transmit data signals received from the medical device to the healthcare provider station during the healthcare sessions or, in certain further aspects thereof, to the caregiver provider station daring the caregiver sessions.

In still another aspect of this embodiment of the invention, the integrated home health system may further include a system management station, coupled to the data network, for authorizing the healthcare provider station to conduct the healthcare sessions with the patient station and for authorizing the caregiver provider station to conduct the caregiver provider sessions with the patient station. In further aspects thereof, the interface device may also enable telehealth sessions between the system management station and the patient station by transmitting video and audio signals, received from the system management station during the telehealth sessions, to the television set for broadcast thereby.

In other aspects of this embodiment of the invention, the integrated home health system may further include an emergency response station coupled to the data network and the PSTN while the patient station further includes an emergency response device coupled to the interface device and the PSTN. In these aspects, the emergency response device is configured for two-way audio exchanges with the emergency response station along a first path which passes through the PSTN and along a second path which passes through the interface device, the broadband access device and the data network. In other aspects thereof, upon receiving, from the emergency response device, a request for connection to the emergency response station, the interface device determines whether the requested connection should be established using the first path or the second path.

DETAILED DESCRIPTION OF THE INVENTION

Figure 1:
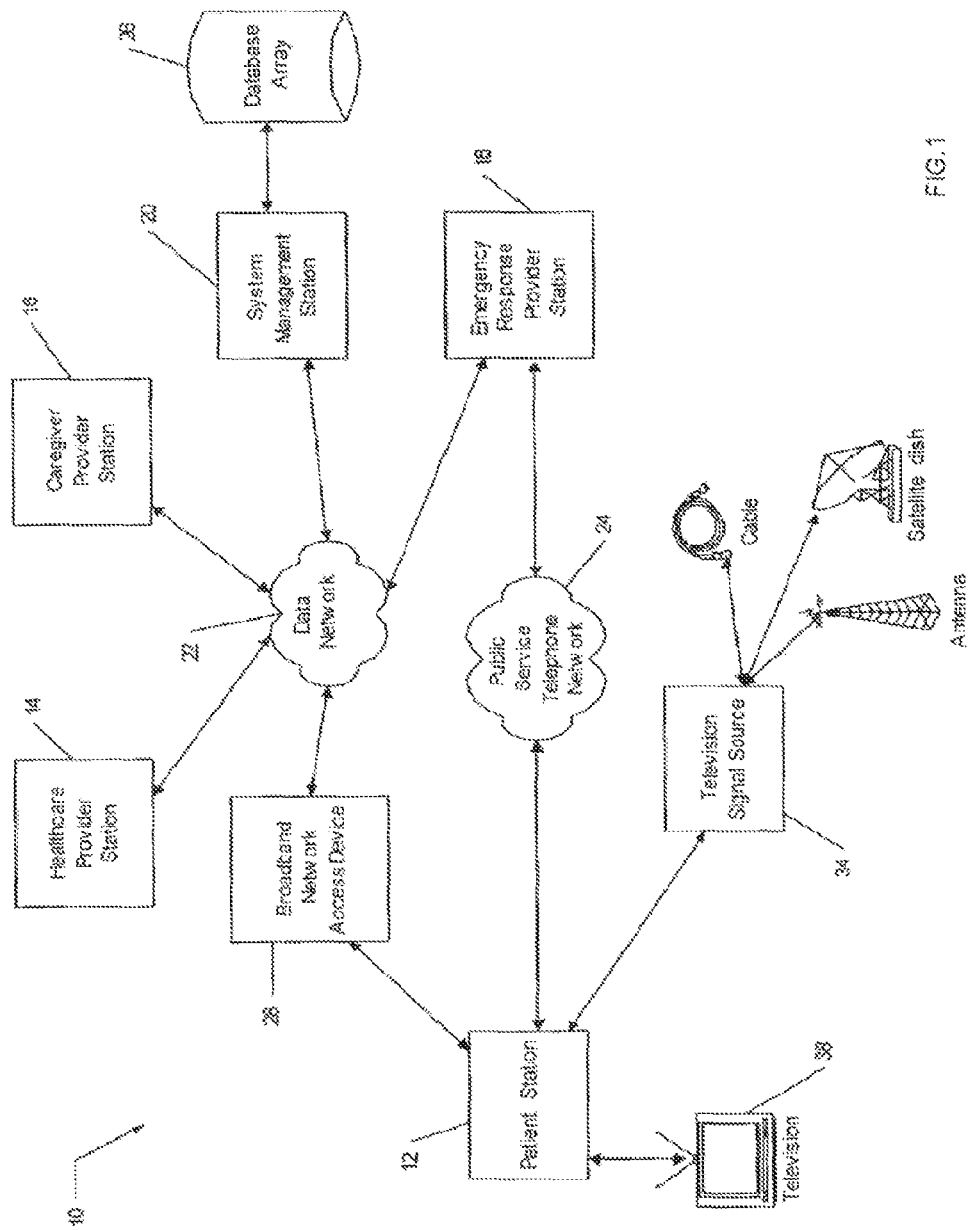
FIG. 1 is a block diagram of an integrated television-based broadband home health system constructed in accordance with the teachings of the present invention.

Referring now to FIG. 1, an integrated television-based broadband home health system 10 constructed in accordance with the teachings of the present invention will now be described in greater detail. As may now be seen, the integrated television-based broadband home health system 10 includes a patient station 12, a first, or healthcare, provider station 14, a second, or caregiver, provider station 16, a third, or emergency response, provider station 18 and a system management station 20 coupled together by a data network 22, for example, the Internet or an interactive television network. As will be more fully described below, each of the first, second and third provider stations 14, 16 and 18 are configured to provide various home health services to a patient located at the patient station 12. As will also be more fully described below, in addition to management operations performed on behalf of the integrated television-based broadband home health system 10, the system management station 20 is also configured to provide various home health services to a patient located at the patient station 12, either alone, or in conjunction with one or more of the first, second and/or third provider stations 14, 16 and 18.

As disclosed herein, the patient station 12 is remotely located relative to each one of the first provider station 14, the second provider station 16, the third provider station 18 and the system management station 20. Similarly, the first provider station 14, the second provider station 16, the third provider station 18 and the system management station 20 are remotely located relative to one another. Of course, it is fully contemplated that, if desired, the integrated television-based broadband home health system 10 may instead be configured such that various ones of the discrete home health services provided by the first provider station 14, the second provider station 16, the third provider station 18 and the system management station 20, respectively, may instead be provided by a common provider station. It is further contemplated that the integrated television-based broadband home health system 10 may instead be configured to include additional provider and/or system management stations. It is contemplated that such additional provider and/or system management stations may be used to provide additional home health services to a patient located at the patient station 12 and/or management services to the integrated television-based broadband home health system 10. It is further contemplated that such additional provider and/or system management stations may be used to provide backup home health services to a patient located at the patient station 12 and/or management services for the integrated television-based broadband home health system 10 in the event of the failure of one or more of the first provider station 14, the second provider station 16, the third provider station 18 and the system management station 20. In any event, it should be clearly understood that the disclosed configuration of the integrated television-based broadband home health system 10 is purely exemplary and that numerous variations of the disclosed configuration are possible while remaining within the scope of the present invention.

The first provider station 14 is a healthcare provider station where healthcare professionals are available to provide home healthcare services to patients remotely located at patient stations such as the patient station 12. Typically, the healthcare provider station 14 would be located at either a physician's office or a healthcare agency or other type of organization responsible for providing home health services to patients at remotely located patient stations. Of course, any number of other locations would be equally suitable for use as the healthcare provider station. The healthcare provider station 14 may be comprised of a computer system, for example, a personal computer (or "PC"), having a plurality of peripheral devices coupled thereto. Software residing on the PC should include an Internet browser, for example, Microsoft Explorer, video conferencing software, for example, Microsoft NetMeeting, and any software applications needed for analyzing and/or displaying raw medical data received from either the patient station 12 or the system management station 20. The peripheral devices coupled to the PC should include a monitor suitable for viewing any video images originating at the patient station 12 or the system management station 20, an audio transmitter system, for example, a speaker system, suitable for reproducing any audio transmissions originating at the patient station 12 or the system management station 20, a digital imager, for example, a webcam, suitable for generating video images to be transmitted to the patient station 12, an audio receiver, for example, a microphone suitable for detecting audible sounds to be transmitted to the patient station 12 and a printer for producing hard copies of desired portions of any medical data displayed on the monitor. It should be clearly understood, however, that the foregoing list of components of and/or peripheral devices coupled to the PC is not intended to be comprehensive and that numerous components thereof and/or peripheral devices coupled thereto have been omitted for ease of description.

As disclosed herein, the home healthcare services which may be provided to a patient located at the patient station 12 from a physician or other healthcare professional located at the healthcare provider station 14 include two-way audio/video consultations, wound care and other diagnostics which typically use digital images, and monitoring of vital signs or other indicators of the health of the patient in both real-time and store-and-forward modes. It is fully contemplated, however, that other home health care services not specifically recited herein may also be provided to the patient located at the patient station 12 from the physician or other healthcare professional located at the healthcare provider station 14. Furthermore, it should be clearly understood that, as will be more fully described below, a typical healthcare session is not necessarily limited to one or more exchanges between the physician or other healthcare professional at the healthcare provider station 14 and the patient located at the patient station 12. Rather, it is contemplated that a healthcare session may also include one or more exchanges between the physician or other healthcare professional located at the healthcare provider station 14 and the system management station 20 and/or one or more exchanges between the patient located at the patient station 12 and the system management station 20. Finally, other stations (not shown), which may provide additional healthcare services to the patient located at the patient station 12, for example, lab systems, insurance systems, pharmacies and the like, may also be linked to the system management station 20.

The second provider station 16 is a caregiver provider station where a family member, close friend or other interested person may periodically check on the health and well-being of a patient located at the patient station 12. While, in the description that follows, the patient located at the patient station 12 has a single caregiver and that the caregiver located at the caregiver station 16 serves in that function for a single patient, it is fully contemplated that a patient may have any number of caregivers and that a caregiver may serve in that function for any number of patients. Typically, the caregiver provider station 16 would be located at the home or office of the family member, close friend or other interested person acting as the caregiver for the patient located at the patient station 12. If desired, however, the caregiver provider station 16 may be suitably located so as to be accessible for use by plural caregivers, each acting as a caregiver for one or more patients located at respective patient stations.

Like the healthcare provider station 14, the caregiver provider station 16 may be comprised of a computer system, for example, a PC, having a plurality of peripheral devices coupled thereto. Software residing on the PC should include an Internet browser, for example, Microsoft Explorer and videoconferencing software, for example, Microsoft NetMeeting. The peripheral devices coupled to the PC should include a monitor suitable for viewing any video images originating at the patient station 12, an audio transmitter system, for example, a speaker system, suitable for reproducing any audio transmissions originating at the patient station 12, a digital imager, for example, a webcam, suitable for generating video images to be transmitted to the patient station 12 and an audio receiver, for example, a microphone, suitable for detecting audible sounds to be transmitted to the patient station 12. It should be clearly understood, however, that the foregoing list of components of and/or peripheral devices coupled to the PC is not intended to be comprehensive and that numerous components thereof and/or peripheral devices coupled thereto have been omitted for ease of description. Furthermore, it is fully contemplated, however, that the caregiver provider station 16 may suitably function without the webcam and/or the microphone. In such configurations, however, the quality of the remote caregiving session would be reduced considerably since, while the caregiver would still be able to monitor the patient and access patient data, for example, vital signs or other health indices of the patient, the patient would no longer be able to look at or hear the caregiver.

The third provider station 18 is an emergency response provider station 18 configured to receive emergency calls originating at the patient station 12. The emergency response provider station 18 is staffed on a 24/7 basis by one or more monitoring personnel trained to handle emergency calls originating at the patient station 12, typically, by conducting a dialogue with the patient located at the patient station 12 and determining, based upon the dialogue with the patient, whether an emergency condition actually exists and, if so, the nature of the emergency. After evaluating an emergency call originating at the patient station 12 in the aforedescribed manner, the monitoring personnel at the emergency response provider station 18 would then dispatch appropriate emergency response personnel to the patient station 12 if necessary.

The emergency response provider station 18 is further configured to receive: (1) non-emergency videoconference calls originating at the patient station 12 and (2) notifications, from the system management station 20, of potential emergency conditions at the patient station 12. If a non-emergency videoconference call is received from the patient station 12, a monitoring personnel at the emergency response provider station 18 would handle the videoconference call and, in the process thereof, determine whether the videoconference call was prompted by an emergency condition at the patient station 12 and whether emergency response personnel should be dispatched to the patient station 12. If a potential emergency notification is received from the system management station 20, the monitoring personnel at the emergency response provider station 18 would determine whether an emergency condition exists at the patient station 12, for example, by conducting a two-way audio exchange with the patient located at the patient station 12 and viewing a digital image, if appropriate. The monitoring personnel at the emergency response provider station 18 would then dispatch appropriate emergency response personnel to the patient station 12 if necessary. It should be noted, however, that a two-way audio exchange is but one way by which monitoring personnel at the emergency response provider station 18 may evaluate conditions at the patient station 12. Under certain conditions, the monitoring personnel will be able to conduct a two-way video/audio exchange with the patient located at the patient station 12. Under other conditions, specifically, when the patient does not respond to an audible inquiry by the monitoring personnel, the monitoring personnel may be able to evaluate conditions at the patient station 12 using a two-way video/audio link, for example, by surveying the patient station 12 to see if the patient has lost consciousness.

While the healthcare and caregiver provider stations 14 and 16 have a single link—the data network 22—to the patient station 12, the emergency response provider station 20 has two possible links to the patient station 12—the first via the data network 22 and the second via public switched telephone network ("PSTN") 24. As will be more fully described below, the patient located at the patient station 12 may request that a connection be established with the emergency response provider station 18 using a variety of techniques, including normal videoconference dialing, actuation of a wired emergency notification device, for example, a panic button, or actuation of a wireless emergency notification device, for example, a neck pendant or wrist-watch style device. Additionally any number of life safety sensors located at the patient station 12 will automatically initiate a request for connection with the emergency response provider station 18 upon detection of an alert condition, for example, when a measured physical parameter exceeds a predetermined threshold value. Life safety sensors which may be located at the patient station 12 or, if appropriate, worn by the patient located at the patient station 12, include smoke detectors, fire detectors, carbon monoxide detectors, wearable physiological sensors, and fall-detection sensors. Upon receipt, from the patient or a life safety sensor, of a request for connection with the emergency response provider station 18, the patient station 12 will first determine whether a link to the emergency response provider station 18 is available via the data network 22. If a data network link is available, the patient station 12 will then proceed to establish a link with the emergency response station 18 over the data network 22. If a data network link is not available, however, the patient station 12 will instead proceed to establish a link with the emergency response provider station 18 over the PSTN 24. As will also be more fully described below, the patient station 12 may select between establishing a connection using the data network or PSTN links based upon any number of criteria. For example, a power failure at the patient station 12 will cause the patient station 12 to establish the link with the emergency response provider station 18 via the PSTN 24.

The system management station 20 provides directory, gatekeeper, and access functionality and performs a wide variety of services for the integrated television-based broadband home health system 10, the patient station 12, the healthcare provider station 14, the caregiver provider station 16 and/or the emergency response provider station 18. As will be more fully described below, these services include, among others, data storage, database management and security services for the integrated television-based broadband home health system 10; life safety, telehealth provider and reminder services for the patient station 12; and potential emergency condition notification services for the emergency response provider station 18. To provide these and other services, the system management station 20 includes a web server (not shown in FIG. 1), one or more application servers (also not shown in FIG. 1) and a database array 26 comprised of one or more databases (also not shown in FIG. 1).

As will be more fully described below, the directory functionality of the system management station 20 involves the maintenance of a wide variety of types of information maintained in the database array 26. The gatekeeper functionality of the system management station 20 involves admission control, bandwidth management, address resolution and directory services, user authentication and authorization, call accounting and call routing functions for H.323 connections. Combined with a proxy service, a gatekeeper provides quality of service ("QoS") capabilities to ensure high-quality H.323 videoconferencing calls over local area network ("LAN") and wide area network ("WAN") infrastructures. The proxy also enhances security by working with firewalls to perform H.323 endpoint address translation. Access functionality which, like directory functionality, is more fully described below, involves the control of access to the resources of the system management station 20, for example, by the healthcare provider station 14 during a home health session.

Briefly, the data storage services provided by the system management station 20 includes storing health-related data collected from or otherwise provided by the patient located at the patient station 12. For example, the health-related data may include data acquired by one or more electronic devices used to measure the vital signs or other health indices of the patient, answers to the questions contained in one or more questionnaires, electronically filled out by the patient, and responses to system and medication reminders for compliance monitoring. The database management services provided by the system management station 20 includes the scheduling of healthcare, caregiver and/or educational sessions for a patient located at the patient station 12 and the scheduling of data collection times at which the vital signs and/or other health indices of a patient located at the patient station 12 are to be measured. The database management services provided by the system management station 20 further includes the scheduling of an appropriate type and number of reminders to be issued in connection with each scheduled session and/or data collection time. The security services provided by the system management station 20 include controlling access to electronic patient records and other confidential information maintained in the one or more databases forming the database array 26, controlling the establishment of connections between a physician or other healthcare professional requesting initiation of a telemedicine or telehealth session between the healthcare provider station 14 and the patient station 12 and controlling the establishment of connections between a family member or other person requesting initiation of a caregiver session between the caregiver provider station 16 and the patient station 12.

The telehealth services which may be provided to a patient located at the patient station 12 by the system management station 20 include various types of education services. For example, the system management station 20 may stream instructional videos, over the data network 22, to the patient station 12, either upon receipt of a request by the patient located at the patient station 12 or by the physician or other healthcare professional located at the healthcare provider station 14. Variously, the educational videos may be streamed on demand or at a pre-arranged time scheduled in advance. It is further contemplated that the educational services provided by the system management station 20 may include interactive educational services, again either upon receipt of a request by the patient located at the patient station 12 or the physician or other healthcare professional located at the healthcare provider station 14, which periodically requires input from the patient, for example, in the form of answers to questions asked by the educational video.

Using the reminder services provided by the system management station 20, the patient located at the patient station 12 may be issued medication reminders intended to remind the patient to take prescription or non-prescription medications or system reminders intended to remind the patient: (1) to measure their vital signs or other indices of their health using various monitoring devices forming part of the patient station 12; (2) of an upcoming telemedicine or telehealth session with a physician or other health care professional located at the healthcare provider station 12; (3) of an upcoming remote caregiving session with a family member or other caregiver located at the caregiver provider station 16; or (4) of an upcoming telehealth session being broadcast by the system management station 20. As will be more fully described below, both medication and system reminders issued by the reminder service of the system management station 20 may be comprised of video messages, audio messages, images, text messages or a combination thereof.

The reminders issued by the reminder service of the system management station 20 may either be of a first type which requires a response or acknowledgement or of a second type which does not require a response or acknowledgement. Of course, if an immediate response to the first type of reminder is not convenient, the patient can temporarily reset the reminder for reissuance after a pre-determined of time. If the patient located at the patient station 12 fails to reset, respond or otherwise acknowledge a reminder requiring a response or acknowledgement, the system management station 20 may notify the emergency response provider station 18 of a potential emergency condition. Conversely, reminders which do not require a response from the patient located at the patient station 12 are typically configured to be broadcast, at the patient station 12, for a pre-determined period of time. At the conclusion of the broadcast, the reminder is typically repeated, either immediately or after a pre-determined time period. The reminder is typically repeated for a pre-determined number of times and then ends.

In conjunction with the reminder service, the system management station 20 maintains compliance records which may be periodically retrieved, for example, by a physician or other healthcare professional located at the healthcare station 14, to determine how well the patient is complying with the various reminders issued by the reminder service of the system management station 20. Typically, the compliance records will maintain a list of the date, time and type of all reminders issued by the system management station 20. The compliance records will also maintain the patient's responses and/or failures to respond to those reminders.

As may be further seen in FIG. 1, the patient station 12 is coupled to the data network 22 by a broadband access device 28. The broadband access device 28 may be a cable modem, a digital subscriber line ("DSL") modem, fixed and/or wireless connections, a satellite data modem, or another broadband data access device. As will be more fully described below, the patient station 12 exchanges Internet protocol ("IP") data packets with the data network 22 via the broadband access device 28.

Figure 2:
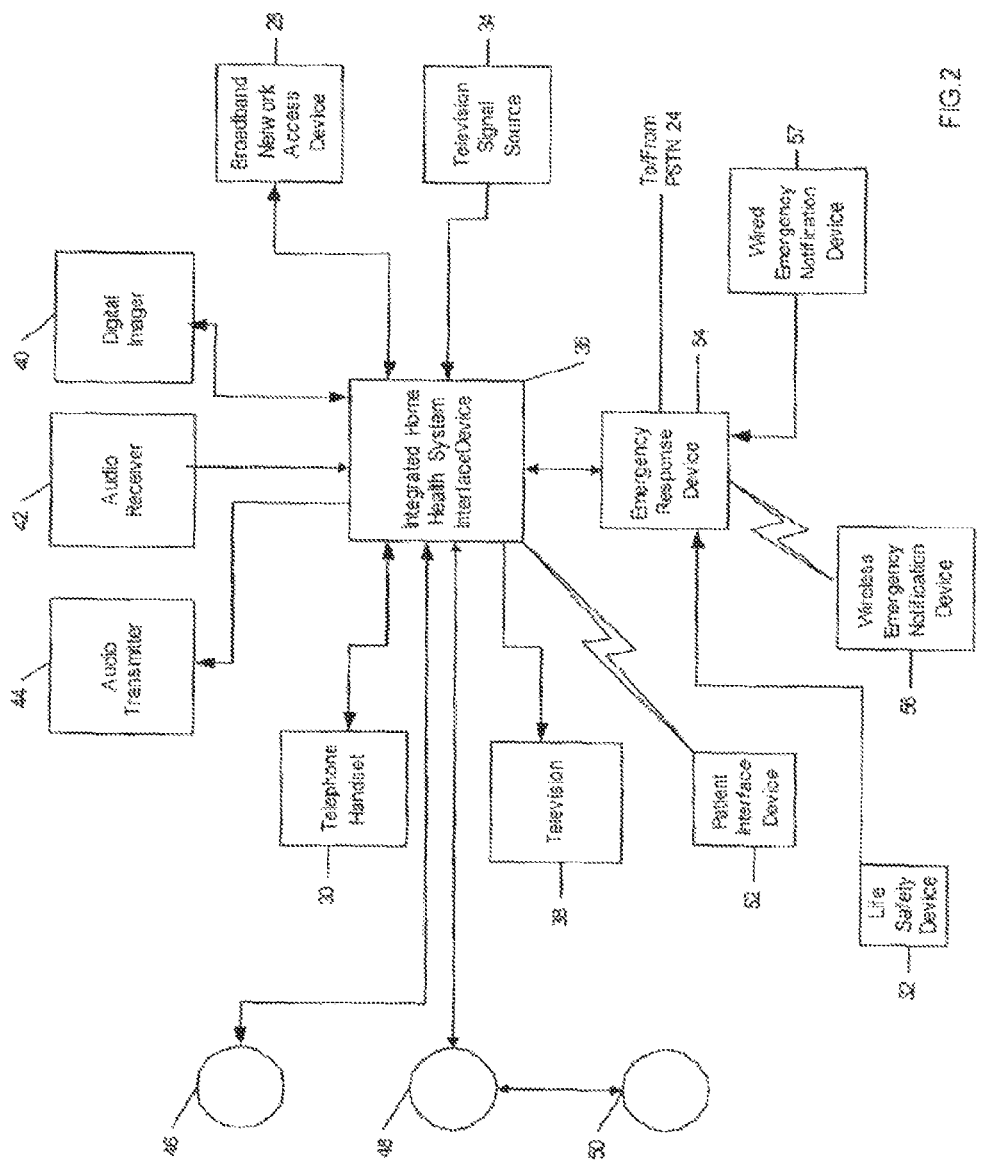
FIG. 2 is a block diagram of a patient station of the integrated television-based broadband home health system of FIG. 1.

Referring next to FIG. 2, the patient station 12 will now be described in greater detail. As may now be seen, a central component of the patient station 12 is an integrated home health system interface device 36 which, as will be more fully described below, enables the delivery of various home health services such as telemedicine, telehealth, caregiver, emergency response and life safety services to a patient located at the patient station 12. While the internal configuration of the integrated home health system interface device 36 will be described in greater detail with respect to FIGS. 3-4, below, the interconnection of the integrated home health system interface device 36 with the broadband access device 28 of the integrated television-based broadband home health system 10 as well as with various other components of the patient station 12 shall first be described.

As may be seen in FIG. 2, the integrated home health system interface device 36 has a first input line coupled to a television signal source 34, an input/output ("I/O") line coupled to the broadband access device 28 and an output line coupled to a TV set 38. The television signal source 34 is an RF modulated composite signal typically provided, as illustrated in FIG. 1, by an antenna, a cable television ("CATV") set top box, or a satellite television service. The television signal source 34 processes the data signals received at the various TV broadcast frequencies into a format suitable for display by TV 38. However, after appropriate processing by the television signal source 34, rather than transmitting the processed signals directly to the TV 38 as is common in the art, the television signal source 34 instead transmits the processed data signals to the integrated home health system interface device 36.

As will be more fully described below, absent contravention resulting from the receipt of certain signals from the broadband access device 28 or other devices forming part of the patient station 12, the integrated home health system interface device 36 will pass the TV broadcast signals received from the television signal source 34 to the TV 38. Contravention, i.e., a temporary interruption of the TV broadcast signals received from the television signal source 34, will occur under a variety of conditions. For example, the initiation of a telemedicine session with a patient located at the patient station 12 by a physician or other health care professional located at the healthcare provider station 14, the initiation of a caregiver session by a family member or other interested person located at the caregiver provider station 16 or the initiation of a telehealth session by the system management station 20 will cause the integrated home health system interface device 36 to temporarily interrupt the passing of TV broadcast signals received on the first input line from the television signal source 34 to the TV 38 in favor of video and audio signals received on the I/O line from the broadband access device 28 as part of the telemedicine, caregiver or telehealth session initiated at the healthcare provider station 14, caregiver provider station 16 or system management station 20, respectively. Variously, the video signals displayed on the TV 38 as part of a telemedicine, caregiver, telehealth or other home health session may produce an image that fills the entire screen, a portion of the screen or, if desired, merely overlays the TV broadcast signal received from the television signal source. The integrated home health system interface device 36 will similarly interrupt the passing of TV broadcast signals received on the first input line from the television signal source 34 to the TV 38 in favor of messages received on the I/O line from the broadband access device 28 as part of the reminder services provided by the system management station 20. Finally, the home health system interface device 36 will interrupt the passing of TV broadcast signals to the TV 38 whenever the patient located at the patient station 12 initiates a home health session using patient interface device 52, for example, a hand-held infra-red ("IR") remote.

In addition to the foregoing devices, a number of other devices are also coupled to the integrated home health system interface device 36. They include a telephone handset 30, a digital imager 40, for example, a camera, an audio receiver 42, an audio transmitter 44, a first medical device 46, a second medical device 48, a third medical device 50 and an emergency response device 54. The digital imager 40, which, for example, may be positioned on a top side surface of the housing of the integrated home health system interface device 36, is coupled to an input line of the integrated home health system interface device and used to capture video images of the patient located at the patient station 12 for viewing at the healthcare provider station 14 during telemedicine, telehealth or other healthcare sessions, for viewing at the caregiver provider station 16 during caregiver sessions or for viewing at the emergency response provider station 18, in order to evaluate whether an emergency condition exists at the patient station 12, during an emergency response session initiated in response to either a notification of a possible emergency by the system management station 20, request for establishment of a videoconferencing connection by the patient located at the patient station 12, initiation of an emergency call by the patient located at the patient station 12 or initiation of a life safety session by a life safety device located at the patient station 12.

The audio receiver 42, for example, a microphone, is coupled to an input line of the integrated home health system interface device 36 and used for detecting audible sounds uttered by the patient located at the patient station 12, typically, as part of one of the aforementioned telemedicine, telehealth, other healthcare, remote caregiving, emergency response or life safety sessions. Conversely, the audio transmitter 44 is coupled to an output line of the integrated home health system interface device and used to generate audible sounds for detection by the patient station 12. Typically, audible sounds generated by the audio transmitter 44 are the same as those generated by the TV 38. However, in the event that the TV 38 has been turned off by the patient located at the patient station 12, the audio transmitter 44 will generate audible messages, for example, reminder messages, for the patient located at the patient station 12. If desired, the TV 38 and the audio transmitter 44 may be configured to operate only in the alternative. In such a configuration, the audio transmitter 44 will operate whenever the TV 38 is turned off but will not generate audible messages when the TV 38 is turned on. If desired, the audio receiver 42 and the audio transmitter 44 may either be discrete devices as illustrated in FIG. 2 or, in the alternative, may be configured as a single device such as a speakerphone. Finally, the telephone handset 30 is used to enhance the privacy of the healthcare, caregiver and other home health sessions conducted at the patient station 12. As previously set forth, in a typical home health session, the TV 38 generates both the video and the audio at the patient station 12. However, should the patient not wish to have their conversation with a home health provider overheard, the patient may activate the telephone handset 30. By doing so, the audio signal generated by the integrated home health system interface device would be rerouted from the TV 38 to the telephone handset 30. As a result, the audio portion of the home health session would no longer be audible, except by the person wearing the telephone handset 30. The telephone handset 30 would also be useful whenever the patient located at the patient station initiated a videoconference, for example, with monitoring personnel at the emergency response provider station 18. Variously, the telephone handset 30 may be configured as a wired device, as illustrated in FIG. 2 or a wireless device (not shown).

Each one of the first, second and third medical devices 46, 48 and 50 are coupled to input lines of the integrated home health system interface device 36 and are used to acquire medical data, typically, measurements of vital signs and/or other indices of the health of the patient located at the patient station 12. As disclosed herein, each one of the first, second and third medical devices are universal serial bus ("USB") devices coupled to USB ports (not shown) forming part of the integrated home health system interface device 36. Depending on the number of USB ports provided on the integrated home health system interface device 36 and the number of medical devices to be coupled to the integrated home health system interface device 36, the medical devices may either be coupled directly to a USB port in a manner similar to the illustrated coupling between the integrated home health system interface device 36 and the first medical device 46 or may be chained to another USB medical device coupled to the USB port in a manner similar to the illustrated coupling between the third medical device 50 and the second medical device 48.

It should be clearly understood the configuration of the patient station 12 illustrated in FIG. 2 in which three medical devices are coupled to the integrated home health system interface device 36 is purely exemplary and that any number of medical devices may be coupled to the integrated home health system interface device 36. Generally, eight medical devices, all of which are commercially available, will cover over 90% of the medical data acquisition needs for the various configurations of the patient station 12 of the integrated television-based broadband home health system 10. These eight devices include a blood pressure device for measuring the blood pressure of the patient located at the patient station 12, a weight scale for measuring the weight of the patient located at the patient station 12, a blood glucose monitor for measuring the blood glucose level of the patient located at the patient station 12, a spirometer for measuring the breathing capacity of the lungs of the patient located at the patient station 12, an electrocardiograph for generating an electrocardiogram ("EKG") showing the variations in electric force which trigger the contractions of the heart of the patient located at the patient station 12, a pulse oximeter for measuring the oxygen level in the blood of the patient located at the patient station 12, a digital camera, preferably, one having resolution of at least one megapixel, for performing remote wound care or other diagnostics requiring high resolution digital imagery and an electronic stethoscope for collecting heart, lung and bowel sounds. Accordingly, it is contemplated that the patient station 12 may be configured to acquire the desired medical data using any combination of these eight or other suitable medical devices.

As further illustrated in FIG. 2, the emergency response device 54 is a discrete device coupled to the integrated home health system interface device 36 and to the PSTN 24. In an alternate configuration of the invention, however, the emergency response device 54 may instead form part of the integrated home health system interface device 36. Regardless, however, an emergency call to the emergency response provider station 18 may be actuated using either a wired emergency notification device 57, for example, a panic button, or a wireless emergency notification device 56, for example, a neck pendant. It is contemplated that the wired emergency notification device 57 may be considerably simpler in configuration than the wireless emergency notification device. In response to actuation of either the wired or wireless emergency notification device 57 or 56, a two-way audio connection is established between the patient station 12 and the emergency response provider station 18. As the wired emergency notification device 57 is physically linked to the emergency response device 54 which, in turn, is physically linked to the integrated home health system interface device 36, it can be safely presumed that the patient actuating the wired emergency notification device is in relatively close proximity to the audio receiver 42 and the audio transmitter 44. Accordingly, the audio receiver 42 and the audio transmitter 44 may be used when establishing the two-way audio connection between the patient station 12 and the emergency response provider station 18. Use of the wireless emergency notification device 56 is contemplated when the patient is no longer in proximity to the emergency response device 54. As a result, the wireless emergency notification device 57 should be equipped with an audio receiver/audio transmitter system, suitable for conducting a two-way audio dialogue therewith.

In one embodiment, one or more life safety devices 32 are also linked to the emergency response device 54. Generally, most life safety devices are configured to automatically detect the presence of a specific type of emergency situation, monitored for such detections on a 24/7 basis and cannot be disarmed readily. For example, fire detectors, smoke detectors, flood detectors, carbon monoxide detectors, wearable physiological sensors and fall-detection sensors may all be deemed to be various types of life safety devices suitable for use as the life safety device 33. Upon detection of an emergency condition, the life safety device 32 transmits a signal to the emergency response device 54 which is handled, by the emergency response device 54, in a manner similar to that used when either the wireless emergency notification device 56 or the wired emergency notification device 57 is actuated. Accordingly, in response to receipt of a signal from the life safety device 32, the emergency response device 54 initiates an emergency call to the emergency response provider station 18. If desired, the emergency response device 54 may also notify the emergency response provider station 18 that the call is being established in response to a detection of the emergency condition by the life safety device 32. By doing so, the monitoring personnel located at the emergency response provider station 18 would be better equipped to evaluate the situation at the patient station 12.

It is contemplated that data to be delivered to the healthcare provider station 14, caregiver provider station 16, emergency response provider station 18 and system management station 20 over the data network 22 may originate at a variety of the devices forming part of the patient care station 12. These devices may include, for example, the digital imager 40, the audio receiver 42, the first medical device 46, the second medical device 48, the third medical device 50, the patient interface device 52, and/or the emergency response device 54. Data received by the integrated home health system interface device 36 from any one or more of the aforementioned devices is passed to the cable modem or other broadband access device 28. In turn, the broadband access device 28 places the data on the data network 22 for delivery to the desired destination.

Figure 3:
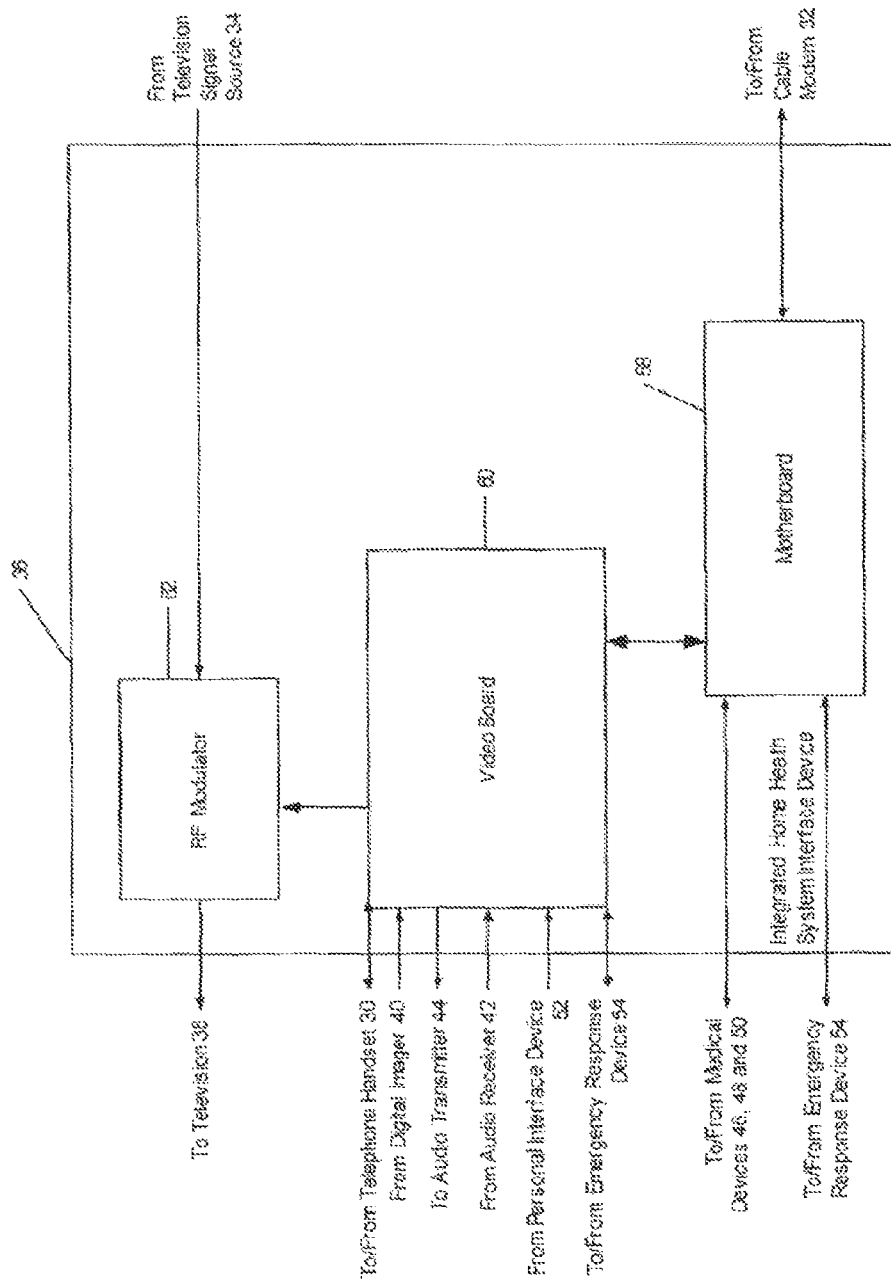
FIG. 3 is a block diagram of an integrated home healthcare interface device of the patient station of FIG. 2.

Referring next to FIG. 3, the integrated home health system interface device 36 will now be described in greater detail. It should be clearly understood that, as illustrated in FIG. 3, the integrated home health system interface device 36 has been greatly simplified for ease of description and that numerous conventional components thereof, for example, the power distribution system, have been omitted from the drawings. As may now be seen, the integrated home health system interface device 36 includes a first processor board 58, a second processor board 60 and a radio frequency ("RF") modulator 62. As will be more fully described below, the first processor board 58, which, for example, may be a low cost, general purpose computing motherboard, is coupled to the cable modem 32 for handling upstream and downstream exchanges of IP data packets with various ones of the healthcare provider station 14, the caregiver provider station 16, the emergency response provider station 18 and the system management station 20. The motherboard 58 is further coupled to the emergency response device 54 for determining, on behalf of the emergency response device 54, the path to be used when issuing an emergency call to the emergency response provider station 18 in response to the detection, by the emergency response device 54, of the actuation of either the wireless emergency notification device 56 or the wired emergency notification device 57. Under certain other conditions, the motherboard 58 will detect the occurrence of a potential emergency condition and notify the emergency response provider station 18 of the same. Finally, the motherboard 58 is also coupled to the first, second and third medical devices 46, 48 and 50 to enable the upload of medical data therefrom.

The second processor board 60, which, for example, may be a video board, is coupled to the motherboard 58 and the RF modulator 42. Of course, while illustrated as a single board, the video board 60 is, in fact, plural board level components which collectively perform the various functionalities disclosed herein. More specifically, the video board 60 receives digital video output signals from the motherboard 58 for transmission to the RF modulator 62. The video board 60 also receives digital audio output signals, again from the motherboard 58, for transmission to the TV 38 and/or the audio transmitter 44. As previously set forth, if the patient located at the patient station 12 activates the telephone handset 30, the digital audio signals which would have been transmitted by the video board 60 to the RF modulator 62 are instead transmitted, by the video board, to the telephone handset 30. The video board 60 also receives audio signals, from the emergency response device 54 for transmission to the audio transmitter 44. The video board 60 further receives video and audio input signals from the digital imager 40 and the audio receiver 42, respectively, for processing and forwarding to the motherboard 58. Under certain conditions, however, the audio signals originating at the audio receiver 42 and received by the video board 60 will instead be destined for the emergency response device 54. Finally, the video board 60 receives data and/or commands from the patient located at the patient station 12 via the patient interface device 52. As will be more fully described below, using the patient interface device 52, the patient may perform a variety of tasks. For example, the patient may review their schedule of appointments and/or reminders, acknowledge the receipt of a reminder, initiate a videoconference with the emergency response provider station 18 or initiate a telehealth session with the system management station 20.

The RF modulator 62 has two input lines, a first coupled to the television signal source 34 and a second coupled to the video board 60. Each one of the television signal source 34 and the video board 60 functions as a source of video and/or audio signals to the RF modulator 62. The signals received from the television signal source 34 are in a format suitable for display by the TV 38. However, the signals received from the video board 60 are not. In the absence of video and/or audio signals from the video board 60, the RF modulator 62 designates the television signal source 34 as the signal source for the TV 38. Accordingly, the RF modulator 62 will pass the signals received from the television signal source 34 to the TV 38. Upon detection of video and/or audio signals from the video board 60, the RF modulator 62 will designate the video board 60 as the signal source for the TV 38. The RF modulator will then convert the video and/or audio signals received from the video board 60 into a format suitable for display by the TV 38 and then pass the converted signals to the TV 38 for display.

Of course, it should be clearly understood that the particular configuration of the integrated home health system interface device 36 disclosed herein is purely exemplary and that numerous modifications may be made thereto while remaining within the scope of the invention. For example, the integrated home health system interface device 36 is disclosed herein as having first and second processor boards 58 and 60. If desired, however, the second processor board 60 may be eliminated by off-loading the functionality residing thereon onto the first processor board 58. Conversely, additional processor boards may be used by offloading selected functionality currently disclosed as residing on either the motherboard 58 or the video board 60 onto a third processor board, for example, a daughter board coupled to either the motherboard 58 or the video board 60. Of course, the interconnections between the various processor boards of the integrated home health system interface device 36 and the interconnections between the integrated home health system interface device 36 and other devices forming part of the patient station 12 may vary depending on the particular functionality offloaded from one processor board to another.

It should be further understood that, rather than the discrete devices illustrated in FIG. 2, certain devices which, together with the integrated home health system interface device 36, form the patient station 12, may, if desired, be incorporated into the integrated home health system interface device 36. For example, in one alternate configuration thereof, the cable modem or other broadband access device 28 is incorporated into the integrated home health system interface device 36. In another, the television signal source 34 is incorporated into the integrated home health system interface device 36. Of course, in still another, both the cable modem or other broadband access device 28 and the television signal source 34 are incorporated into the integrated home health system interface device 36. Such a configuration would have considerable appeal to consumers attracted to those configurations of the invention which require only a single "box" between the cable outlet or other source of the RF modulated composite TV signal and the TV 38. Finally, in still yet another configuration, the integrated home health system interface device 36 may be configured such that the emergency response device 54 is a component thereof. In such a configuration, the integrated home health system device 36 would include a third processor board, coupled to both the motherboard 58 and the video board 60, on which the functionality of the emergency response device 54 resides.

Figure 4:
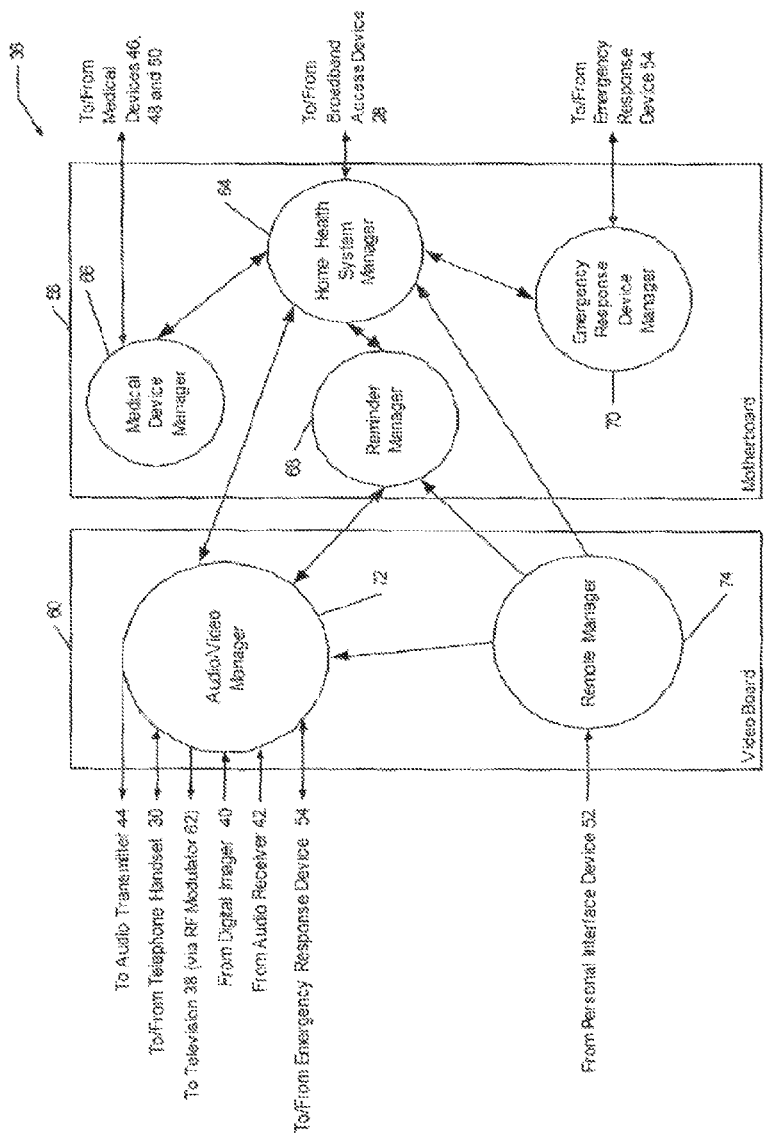
FIG. 4 is a functional block diagram of the integrated home healthcare interface device of FIG. 3.

Referring next to FIG. 4, the functionality residing within the integrated home health system interface device 36 will now be described in greater detail. As may now be seen, residing on each of the motherboard 58 and the video board 60 are plural managers, each of which provides a discrete functionality to respective ones of the motherboard 58 and the video board 60. Each manager residing on either the motherboard 38 or the video board 60 may be embodied in hardware, software or a combination thereof. The plural managers residing on the motherboard 58 include a first, or home health system, manager 64, a second, or medical device, manager 66, a third, or reminder, manager 68 and a fourth, or emergency response device, manager 70. The plural managers residing on the video board 60, on the other hand, include a first, or audio/video, manager 72 and a second, or remote, manager 74.

Turning first to the plural managers residing on the motherboard 58, the home health system manager 64 handles downstream and/or upstream exchanges between the cable modem 32 and the various managers residing on either the motherboard 58 or the video board 60, more specifically, the medical device manager 66, the reminder manager 68, the emergency response device manager 70, the audio/video manager 72 and the remote manager 74. The medical device manager 66 handles the issuance of commands to and the acquisition of data from the first, second and third medical devices 46, 48 and 50. More specifically, each of the first, second and third medical devices 46, 48 and 50 may forward acquired medical data to the medical device manager 66 in either "store-and-forward" or "real-time" modes. In the store-and-forward mode, the patient periodically collects medical data, typically, either on their own volition or in response to the issuance of a reminder by the reminder service of the system management station 20.

During the collection of medical data, the first, second and third medical devices 46, 48 and 50 may or may not be coupled to the integrated home health system interface device 36. If coupled to the integrated home health system interface device 36, the medical device manager 66 will have instructed the first, second and third medical devices 46, 48 and 50, respectively, to forward all medical data to the medical device manager 66 upon the acquisition thereof. Accordingly, upon the acquisition of medical data by one or more of the first, second and third medical devices 46, 48 and 50, the acquired data is promptly forwarded by the medical device to the medical device manager 66. The medical device manager 66 passes the acquired data to the home health system manager 64 which, in turn, forwards the acquired data to the cable modem 32 for upstream transfer, via the data network 22 to the system management station 20 for storage thereat in a selected database forming part of the database array 26. Conversely, if the first, second and third medical devices 46, 48 and 50 are not coupled to the integrated home health system interface device 36, data acquired by the first, second and third medical devices will be held in a local memory thereof until they are subsequently coupled to the integrated home health system interface device 36. Upon coupling thereto, the medical device manager 66 will issue a command to the first, second and third medical devices which causes them to initiate a dump of the medical data acquired thereby to the medical device manager 66. Subsequent handling of the medical data received by the medical device manager 66 will then proceed in the manner hereinabove described.

Acquisition of medical data in real-time mode is typically performed in conjunction with a telemedicine session initiated by a physician or other healthcare professional located at the healthcare provider station 14. As part of the part of the telemedicine session, and in conjunction with oral instructions transmitted to the patient located at the patient station over the two-way video/audio link, the physician or other healthcare professional will issue an instruction to the system management station 20 to initiate a real-time collection of specified types of medical data. In turn, the system management station 20 will issue an instruction to the medical device manager 66, again, via the home health system manager 64, to begin real-time data collection for the specified types of medical data. The medical device manager 66 selects appropriate ones of the first, second and third medical devices 46, 48 and 50 which are configured to collect the specified types of medical data and issues instructions to the selected ones of the first, second and third medical devices 46, 48 and 50 to begin collection of the medical data. As the selected ones of the first, second and third medical devices 46, 48 and 50 begin to acquire medical data from the patient located at the patient station 12, the acquired medical data is transported to the home health system manager 64 in the manner previously described and, from the home health system manager 64, is transferred upstream, via the cable modem 32 and the data network 22, to both the healthcare provider station 14 for inclusion in a real-time display and to the system management station 20 for storage in the database 26. The real time data acquired using the selected ones of the first, second and third medical devices 46, 48 and 50 may be of either a single reading of the acquired type of medical data or a continuous reading of the acquired type of medical data. Of the various devices previously identified as typical medical devices suitable for use as any one of the first, second and third medical devices 40, 48 and 50, the blood pressure monitor, the blood glucose monitor and the spirometer are among those medical devices used to acquire a single reading for a type of medical data while the electrocardiograph and the pulse oximeter are among those medical devices used to acquire a continuous reading which extends over a period of time for a type of medical data.

When the system management station 20 determines that a reminder should be issued at the patient station 14, a request for generation of a reminder message is issued by the system management station 20. The request is transported to the home health system manager 64 via the data network 22 and the cable modem 32 and, in turn, is passed to the reminder manager 68. Upon receipt of the request, the reminder manager 68 issues a command to the audio/video manager 72 to begin generation of a reminder message. The audio/video manager 72 generates a reminder message comprised of video and/or audio signals and transports the generated video and/or audio signals to the TV 38 and/or the audio transmitter 44 so that the reminder message may be viewed and/or heard by the patient located at the patient station. Further details of the disclosed method for generating reminder messages is set forth in greater detail with respect to FIG. 9, below.

As previously set forth, reminder messages generated by the audio/video manager 72 may require that the patient located at the patient station 12 reply to or otherwise acknowledge viewing and/or bearing the reminder message. If so, the patient located at the patient station 12 replies to or otherwise acknowledges the remainder message using the patient interface device 52, for example, by actuating a "reminder received" button on the patient interface device 52. Signals issued by the patient interface device 52 are analyzed by the remote manager 74. If the remote manager 74 determines that the signal issued by the patient interface device 52 indicates that the patient viewed and/or heard the reminder message, the remote manager 74 forwards a "reminder received" message to the reminder manager 68. If the reminder manager 68 receives the reminder message within a pre-selected period of time after issuance of a reminder, the reminder manager 68 concludes that the reminder was received by the patient located at the patient station 12. Conversely, if the reminder manager 68 fails to receive the reminder message within the pre-selected time period, the reminder manager 68 concludes that the reminder was not received by the patient located at the patient station 12. As before, further details as to how the disclosed method for generating reminders proceeds upon determining that a reminder message was either received or not received by the patient located at the patient station 12 is set forth in greater detail with respect to FIG. 9, below.

The emergency response device manager 70 receives emergency calls originating at the emergency response device 54 and, as is more fully described below with respect to FIG. 8a, determines the type of connection to be established between the emergency response device 54 and the emergency response provider station 18. If the emergency response device manager 70 determines that a data network connection is to be established, the emergency response device manager 70 initiates establishment of the connection by issuing a request for connection to the home health system manager 64. Conversely, if the emergency response device manager 70 determines that a PSTN connection is to be established, the emergency response device manager 70 returns a message to the emergency response device 54 instructing the emergency response device 54 to initiate a request for connection to the emergency response provider station 18 over the PSTN 24.

Turning next to the plural managers residing on the video board 60, the audio/video manager 72 handles video signals to be used in generating images for display on the TV 38 and/or audio signals to be used in reproducing audible sounds using either the TV 38 and/or the audio transmitter 44. It is contemplated that the aforementioned video and/or audio signals may originate from a variety of sources. For example, during a telemedicine, telehealth or other healthcare session initiated by a physician or other healthcare professional located at the healthcare provider station 14, video images and audible sounds respectively detected by a webcam and microphone at the healthcare provider station 14 are converted into video and audio signals, respectively, and transported via the Internet 22 and the cable modem 32 to the home health system manager 64. In turn, the home health system manager 64 transfers the video and audio signals to the audio/video manager 72 where a series of video images and/or audible sounds are generated from the received video and/or audio signals, respectively. Similarly, video images and audible sounds respectively detected by a webcam and microphone at the caregiver provider station 16 are converted into video and/or audio signals in the same manner and transported to the audio/video manager 72, again for generation of a series of video images and audible sounds therefrom. Streaming video, originating at the system management station 20, for example, in response to initiation of a telehealth session by a physician or other healthcare professional at the healthcare provider station 14, is similarly transported to the audio/video manager 72 for generation of a series of video images and audible sounds therefrom.

As previously set forth, the reminder manager 68 attends to the transfer of reminder messages, some of which require a response or acknowledgement of receipt thereof, to the audio/video manager 72 for the generation of video and/or audio reminder messages therefrom. As further previously set forth, various control signals may be generated by the patient located at the patient station 12 using the patient interface device 52. A first control signal which may be generated by the patient interface device 52 indicates that the reminder message was received. Accordingly, in response to receipt of the first control signal, the remote manager 74 issues a return message, to the reminder manager 68, advising the reminder manager 68 that the reminder message was received. Based upon whether a reminder message requires a response or acknowledgement thereof and whether a return message was received from the remote manager 74, the reminder manager 68 will determine whether to issue a notification, to the emergency response provider station 18, of a potential emergency condition at the patient station 12. If the reminder manager 68 determines to issue such a notification, the notification is passed to the home health system manager 64 for upstream transmission over the cable modem 32 and the Internet 22. Finally, and as will be more fully described below with respect to FIG. 7, below, if the signal generated by the patient interface device 52 and received by the remote manager 74 is a second control signal, the remote manager 74 will issue an instruction to the audio/video manager 72 to display selected ones of a plurality of screenings illustrating the various controls which may be actuated by the patient located at the patient station 12 using the patient interface device 52.

It should be readily appreciated by one skilled in the art that various ones of the functionalities herein identified as residing within the plural managers residing on a first one of the pair of processor boards 58 and 60 may, if desired, reside on the other one of the pair of processor boards 58 and 60. It should be further appreciated that all of the functionalities identified as residing within the plural managers residing on one or the other of the pair of processor boards 58 and 60 may instead reside on a single, unified, processor board which incorporates all of the functionality herein described as residing within the integrated home health system interface device 36. Finally, it should be appreciated that plural ones of the disclosed managers may, if desired, be combined into a single, common, manager which incorporates the functionality of the plural ones of the disclosed managers combined into the single, common, manager.

Figure 5:
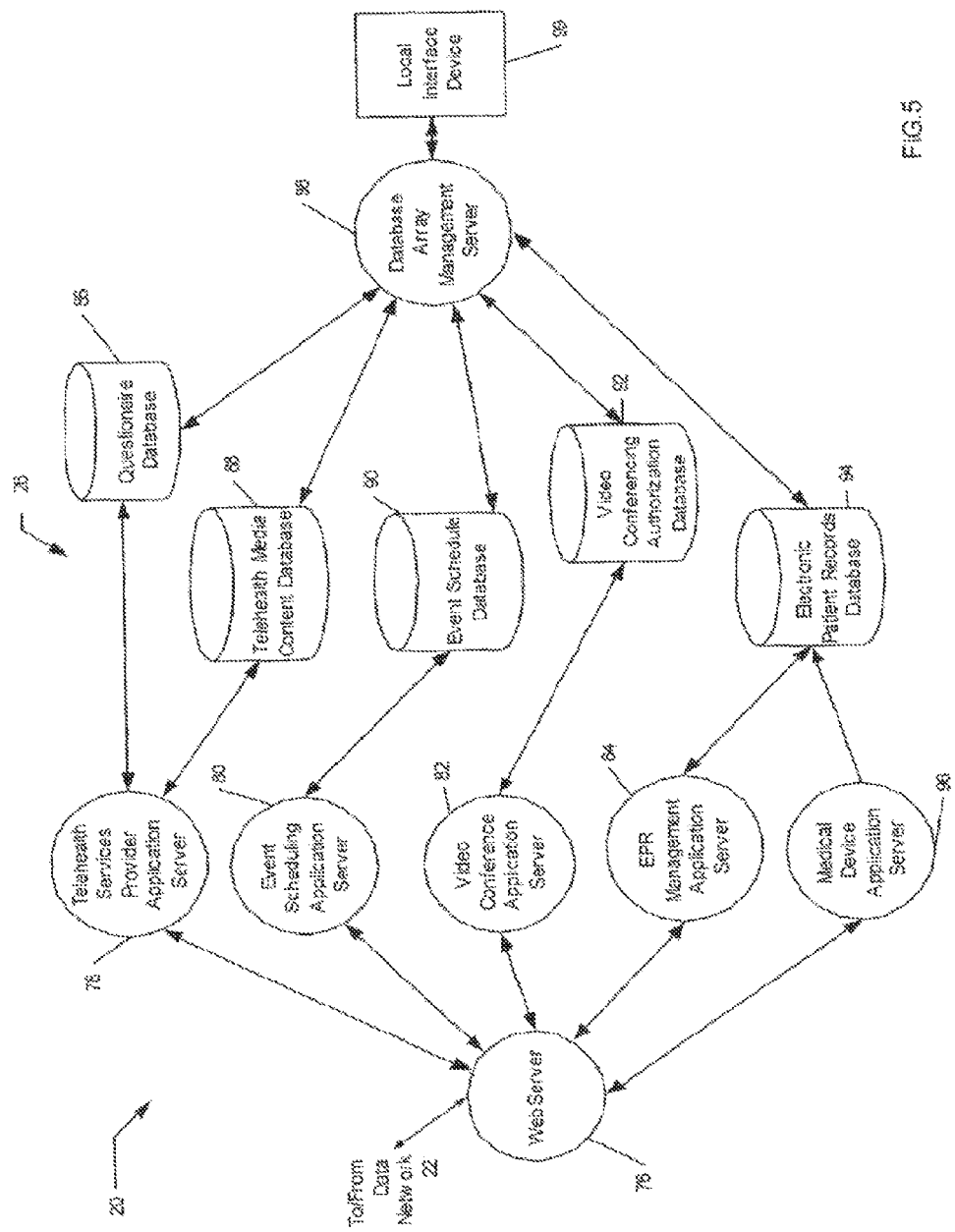
FIG. 5 is a block diagram of a system management station of the integrated television-based broadband home health system of FIG. 1.

Referring next to FIG. 5, the system management station 20 will now be described in greater detail. Again, it should be clearly understood that, as illustrated in FIG. 5, the system management station 20 has been greatly simplified and that various components of the system management station 20 not deemed necessary for an understanding of the present invention have been omitted from the drawing for ease of description. As may now be seen, the system management station 20 includes plural servers, specifically, web server 76, telehealth services provider application server 78, event scheduling application server 80, video conferencing application server 82, electronic patient record ("EPR") management application server 84, medical device application server 96 and database array management server 96 and plural databases, specifically, questionnaire database 86, telehealth media content database 88 event schedule database 90, video conferencing authorization database 92 and electronic patient records database 94, which collectively comprises the database array 26. As disclosed herein, a discrete application resides on each of the application servers 78, 80, 82 and 84. It is fully contemplated, however, that, in one embodiment of the invention, plural ones of these applications may reside on a common server. As further disclosed herein, a separate category of data is stored on each of the databases 86, 88, 90, 92 and 94. It is further contemplated, however, that in one embodiment of the invention, plural, ones of these types of data may be stored in a common database.

The web server 76 maintains content which may be viewed by users accessing the web server 76 via the Internet. Using a web browser residing on the computer system respectively located thereat, the web server 76 may be accessed via the data network 22 from the healthcare provider station 14, the caregiver provider station 16 or the emergency response provider station 18 of the integrated television-based broadband home health system 10. The web server 76 may also be accessed from the patient station 12 using the home health system manager 64. The telehealth services provider application server 78, the event scheduling application server 80, the video conferencing application server 82, the EPR management application server 84 and the medical device application server 96 all function in support of the web server 76. Accordingly, if the user accessing the content maintained by the web server 76 executes a selected one of the application servers 78, 80, 82, 84 and 86, the web server 76 would transport the user's commands to the selected one of the application servers 78, 80, 82, 84 and 86 for execution.

Various ones of the commands transported to the application servers 78, 80, 82, 84 and 86 may involve a read or write operation to a selected one of the databases 86, 88, 90, 92 and 94. For such commands, the selected one of the application servers 78, 80, 82, 84 and 86 would access the selected one of the databases 86, 88, 90, 92 and 94 and execute the operation. Others of the commands transported to the application servers 78, 80, 90, 92 and 94 may involve initiating an action at the patient station 12. For such commands, the selected one of the application servers 78, 80, 82, 84 and 86 would generate a command message initiating the action at the patient station 12 and transfer the generated command message to the home health system manager 64 via the web server 70, the data network 22 and the cable modem 32. Still others of the commands may involve both an access to one of the selected databases 86, 88, 90, 92 and 94 and, using the information obtained from the accessed database, initiating an action at the patient station 12. After executing the command, the selected one of the application servers 78, 80, 82, 84 and 86 would return the results to the web server 76 for viewing by the user. Of course, the content which allows a user to execute commands using one or more of the application servers 78, 80, 82, 84 and 86 is restricted content. Accordingly, prior to allowing a user access to the restricted content, the web server 76 would first redirect the user to an access server (not shown) for execution of an authentication and/or authorization session and, only upon authentication and/or authorization thereof, would the web server 76 allow the user access to the restricted content which allows the user to execute commands using a selected one of the application servers 78, 80, 82, 84 and 86.

The telehealth services provider application 78 provides various telehealth services to a patient located at the patient station 12. One such telehealth service provided by the telehealth services provider 78 is educational services. More specifically, various educational programs are stored in the telehealth media content database 88. If the patient wishes to view one of these programs, the patient would access the telehealth services provider application server 78 through the web server 76, view a list of available programs stored in the telehealth media content database 88 and select a program to be transmitted to the patient station 12. The telehealth services provider application 78 would then retrieve the selected program from a location within the telehealth media content database 88 and stream the selected program to the patient station 12. Of course, it is contemplated that the telehealth media content database 88 may also maintain interactive programs which periodically require user feedback and which vary the content subsequently transmitted to the user based upon that feedback. In addition to transmitting a selected educational program in response to a request by the patient located at the patient station, educational programs may also be scheduled in advance, for example, by a physician or other healthcare professional located at the healthcare provider station 14 or a caregiver located at the caregiver provider station 16. If scheduled in advance, the event scheduling application server 80 would issue a message to the telehealth services provider application server 78 at the time when the program is to be transmitted. The message transmitted to the telehealth services provider 78 would identify the program to be transmitted and specify the destination for the transmission. The telehealth services provider application server 78 would then attend to retrieval of the identified program from the telehealth media content database 88 and the subsequent transmission of the identified program to the specified destination.

Another telehealth service provided by the telehealth services provider 78 is collection of information, typically medical in nature, from patients. More specifically, various medical questionnaires are stored in the questionnaire database 86 and may be retrieved therefrom by the telehealth services provider application server 78 for viewing by a patient located at the patient station 12. For example, a physician or other healthcare provider at the healthcare provider station 14 may, during a healthcare session with a patient located at the patient station 12, request that the patient answer a questionnaire. The physician or other healthcare professional may then access, through the web server 76, the telehealth services provider application server 78, obtain a list of questionnaires stored in the questionnaire database 86 and select a questionnaire to be transmitted to the patient station 12. The telehealth services provider application server 78 would then retrieve the selected questionnaire program from a location within the questionnaire database 86, and transmit the selected questionnaire to the patient station 12. Responses returned from the patient station 12 would be forwarded by the web server 76 to the EPR management application server 84 for entry at a specified location in the electronic patient records database 94.

The event scheduling application server 80 may be used to schedule various types of events, for example, telemedicine, telehealth, or caregiver sessions for the patient located at the patient station 12. Another type of event which may be scheduled using the event scheduling application server 80 are reminders of any of the aforementioned types of events. A user, for example, a physician or other healthcare professional located at the healthcare provider station 14, scheduling an event would access the event scheduling application server 80 through the web server 76. The user would then generate an entry for storage in the event schedule database 90. Typically, such an entry would include the type of event, the time at which the event is to occur, and the location of the event. Preferably, the entries maintained in the event schedule database 90 would be sortable by both the time at which the event shall occur and the patient for which the event has been scheduled. By doing so, a subsequent user accessing the event scheduling application server 80, for example, a caregiver located at the caregiver provider station 16 may review the schedule of events for the patient and may avoid scheduling a prospective remote caregiving session at a time which conflicts with a previously scheduled healthcare session.

Additionally, the event scheduling application server 80 periodically checks the contents of the event schedule database 90 for entries which, based upon the time at which they are scheduled to occur, need to be executed. If the event scheduling application server 80 locates an entry related to an event which is scheduled to occur within a pre-selected period of time, the event scheduling application server 80 retrieves the entry from the event schedule database 90 for execution. Of course, the process used to execute the entry will vary depending on the particular type of entry that was retrieved. For example, if the entry was a reminder, the event scheduling application server 80 would generate a reminder message for transmission to the patient station 12. If, however, the entry indicated that a telehealth session had been scheduled, the event scheduling application server 80 would notify the telehealth services provider application server 78 of the particular video or questionnaire to be transmitted to the patient station 12 or other type of educational session to be initiated. The telehealth services provider application server 78 would then retrieve the appropriate video, questionnaire or other appropriate content from either the questionnaire database 86 or the telehealth media content database 88 and attend to the transmission of the retrieved content to the patient station 12 in the manner previously described.

The video conference application server 82 serves to authenticate and/or authorize users who desire to initiate a two-way video/audio conference with the patient located at the patient station 12. For example, if a caregiver located at the caregiver provider station 14 wishes to initiate a remote caregiving session, the caregiver would first access the video conference application server 82 through the web sever 76. The caregiver would then provide identifying information, for example, a user name and/or password to the video conference application server 82. In turn, the video conference application server 82 would compare the provided identifying information to a list of authorized persons maintained in the video conference authorization database 92. Typically, the video conference authorization database 92 would include a series of entries, each identifying a user who is authorized to conduct a healthcare or remote caregiving session and the pattern with whom the user is authorized to conduct such a session. Preferably, each entry would also identify the level of access to the patient station 12 granted to that user. For example, the various users requesting sessions may variously be granted two-way audio transmission rights, two-way video transmission rights, medical device data acquisition rights or the combination of all three. The video conferencing application server 82 may also place a time limit on the rights granted. For example, while it is expected that a physician or other health care professional would not have any time limits placed on the rights granted thereto, it may be desirable to limit the duration of access rights granted to caregivers, thereby limiting the duration of remote caregiving sessions. After determining the rights to be granted and/or time limit placed thereon, the videoconference application server would, subject to the determined limitations, establish the requested session.

The EPR management application server 84 serves to manage electronic patient records maintained in the electronic patient records database 96. For example, a physician or other healthcare professional located at the healthcare provider station 14 may access the EPR management application server 84 through the web server 76, view a list of patient records maintained in the electronic patient record database 94 and select a patient record for review. Once retrieved, the physician or other healthcare professional may also add additional information to the electronic patient record. For example, a physician or other healthcare professional 14 who retrieved the electronic patient record for a patient in connection with a telemedicine or other healthcare session may wish to add a diagnosis, course of treatment, protocols, response to protocols and other notes to the electronic patient record either during or at the conclusion of the telemedicine or other healthcare session. Typically, the electronic patient records database is comprised of a series of entries, each corresponding to a patient being served by the integrated television-based broadband home health system 10. Included in each entry would be identifying information for a patient, the location of the patient station for that patient, a list of sessions conducted or other contacts with the patient and a record of all events.

The medical device application serves 96 controls the writing of acquired medical data from the patient station 12. As previously set forth, whenever medical data for a patient is acquired from the first, second and third medical devices 46, 48 and 50 located at the patient station 12, all such medical data is transferred, via the web server 76 to the medical device application server 96. The medical device application server 96 decrypts the received medical data, parses the decrypted medical data and then writes the parsed medical data for to an entry maintained in the electronic patient records database 94 for that patient. The medical device application server 96 then transmits an acknowledgement to the home health system manager 64 which, in turn, instructs the medical device manager 66 to issue an instruction to the medical device from which the medical data now stored in the electronic patient record database 94 originated to clear its local memory.

Various administrative functions for the system management station may be performed by a system administrator using the database array management server 98, typically, using a local interface device 99 such as computer system having a monitor, keyboard and mouse. For example, whenever a new patient is added, the system administrator may create an initial patient record, typically, containing only identifying information for the patient and the location of the patient station 12 for the patient, in the electronic patient records database. Similarly, other tasks commonly performed by the system administrator would include modifying the list of persons authorized to conduct healthcare or caregiver sessions maintained in the video conferencing authorization database 92, adding or editing programs maintained in the telehealth media content database 88 and adding or editing questionnaires maintained in the questionnaire database 86.

Figure 6:
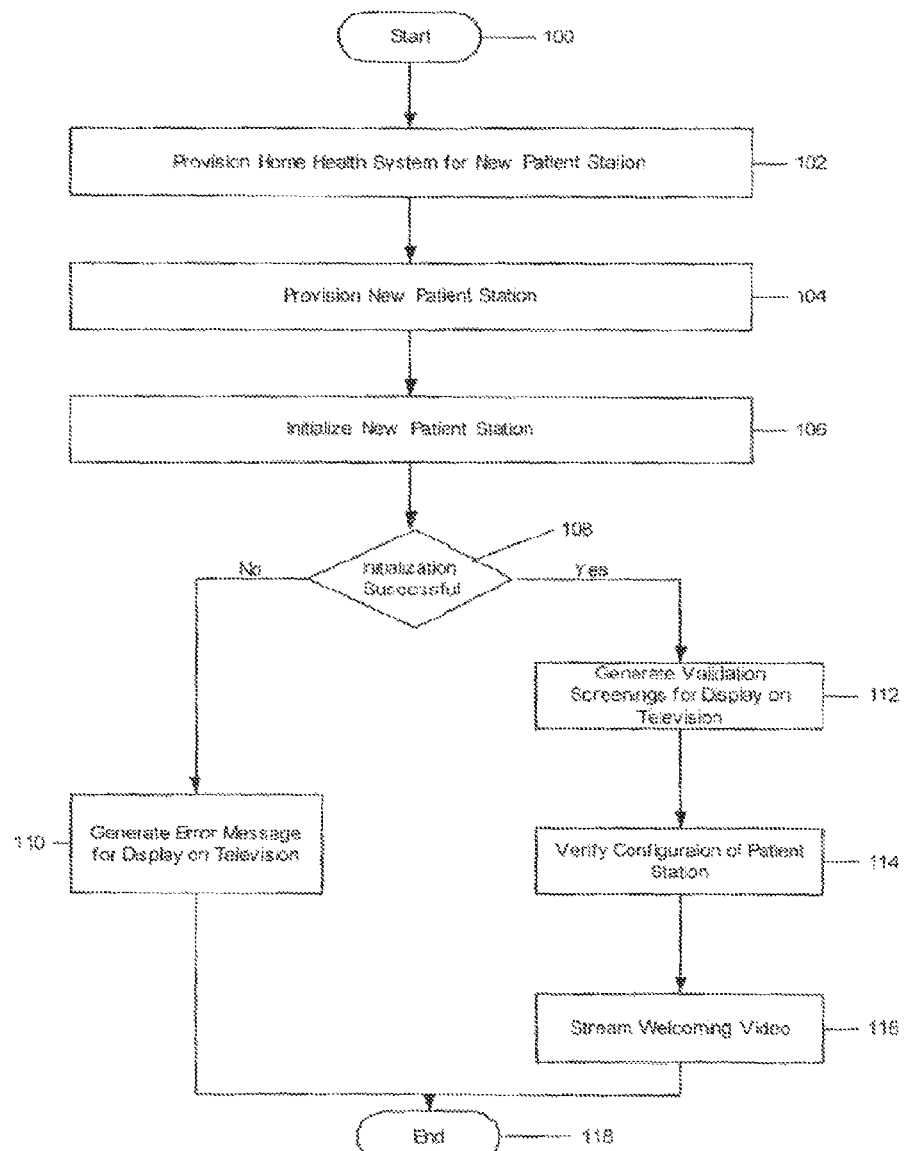
FIG. 6 is a flowchart of a method for installing the patient station of FIG. 2 into the integrated television-based broadband home health system of FIG. 1.

Referring next to FIG. 6, a method of provisioning an existing television-based integrated broadband home health system, for example, the television-based integrated broadband home health system 10, for a new patient station, for example, a patient station similarly configured to the patient station 12, will now be described in greater detail. The method commences at step 100 and, at step 102, the integrated television-based broadband home health system is provisioned for the new patient station. To do so, the electronic patient records database 94 must be modified to add an additional patient record for the describing the patient located at the new patient station to the series of electronic patient records maintained in the electronic patient records database 94. For example, the database array management server 96 may created an additional electronic patient record within the available space of the electronic patient records database 94. While, as previously set forth, a wide variety of information is maintained in the electronic patient record for a patient, upon initial provisioning of the new patient station, the electronic patient record to be added to the electronic patient records database 94 may initially be limited to basic patient identification information. Typically, the initial provisioning of the new patient station will also include creating an authorization record in the video conferencing database 92 which identifies each healthcare provider station 14 authorized to conduct telemedicine, telehealth or other healthcare sessions with the newly added patient station using two-way video/audio conferencing over the data network 22. The authorization record would further identify each caregiver provider station 16 authorized to conduct remote caregiving sessions with the newly added patient station, again using two-way video/audio conferencing over the data network 22. If desired, rather than merely identifying the authorized healthcare and caregiver provider stations 14 and 16, the authorization record may further identify the person or persons who may initiation such sessions at the healthcare and caregiving stations 14 and 16, respectively.

Upon provisioning the integrated television-based broadband home health system 10 at step 102, the method proceeds to step 104 for provisioning of the newly added patient station. Unlike the data provisioning at step 102, step 104 involves the provisioning of the physical equipment to form part of the newly added patient station. Typically, the physical provisioning of the newly added patient station would involve the CATV service provider to install a cable modem and set top box at the location of the newly added patient station. The CATV service provider would then install a television-based integrated broadband home health system interface device between the set top box and the TV. Finally the medical and other peripheral devices forming part of the newly added patient station would be plugged into the television-based integrated broadband home health system interface device.

Upon completing the physical provisioning of the newly added patient station, the method proceeds to step 106 where the newly added patient station is initialized. Once powered up, the television-based integrated broadband home health system interface device will receive an IP address and then attempt to contact the system management station 20 to perform the initialization process. Continuing on to step 108, if an IP address is not received and/or communication with the system management station 20 fails, it is determined that initialization of the newly added patient station has failed and the method proceeds to step 110 where and error message is generated, by the television-based integrated broadband home health system interface device, for display on the TV. The method then ends at step 118.

Returning to step 108, if communication with the system management station 20 is established, it is determined that initialization of the newly added patient station has been successful and the method proceeds to step 112 where the web server 76 issues an instruction to the EPR management application server 84 to access the electronic patient records database 94 to display the electronic patient record entered at step 102 for the newly added patient station. The web server 76 displays the electronic patient record for the newly added patient station, typically, as a series of screens of data and asks that the patient located at the newly added patient station to confirm the accuracy of the electronic patient record. By confirming the accuracy of the electronic patient record, the electronic patient record is deemed to have been validated.

The method then proceeds to step 114 where the configuration of the newly added patient station 12 is verified. To do so, the television-based integrated broadband home health system interface device will identify each peripheral plugged into its USB ports and confirm various ones of its settings, for example, the date and the time of day. The identity of the peripherals plugged into the television-based integrated broadband home health system interface device is transferred to the web server 76 which, in turn instructs the EPR management application server 84 to update the electronic patient record for the newly added patient station to include the identity of each peripheral device coupled to the newly added patient station. By doing so, the configuration of the newly added patient station is verified and the method proceeds to step 116 where the telehealth services provider application server 78 retrieves an introductory video from the telehealth media content database 88 and streams the retrieved video over the data network 22 where it is displayed on the TV of the newly added patient station. It is contemplated that the introductory video will provide guidance on the basic operation of the patient station 12, instruct the patient how to use the various medical devices coupled to the television-based integrated broadband home health system interface device 36 and teach the patient how to use the patient interface device 52 to control various operations of the patient station 12. Having completed the provisioning of an existing television-based integrated broadband home health system to include a newly added patient station, the method ends at step 118.

Figure 7:
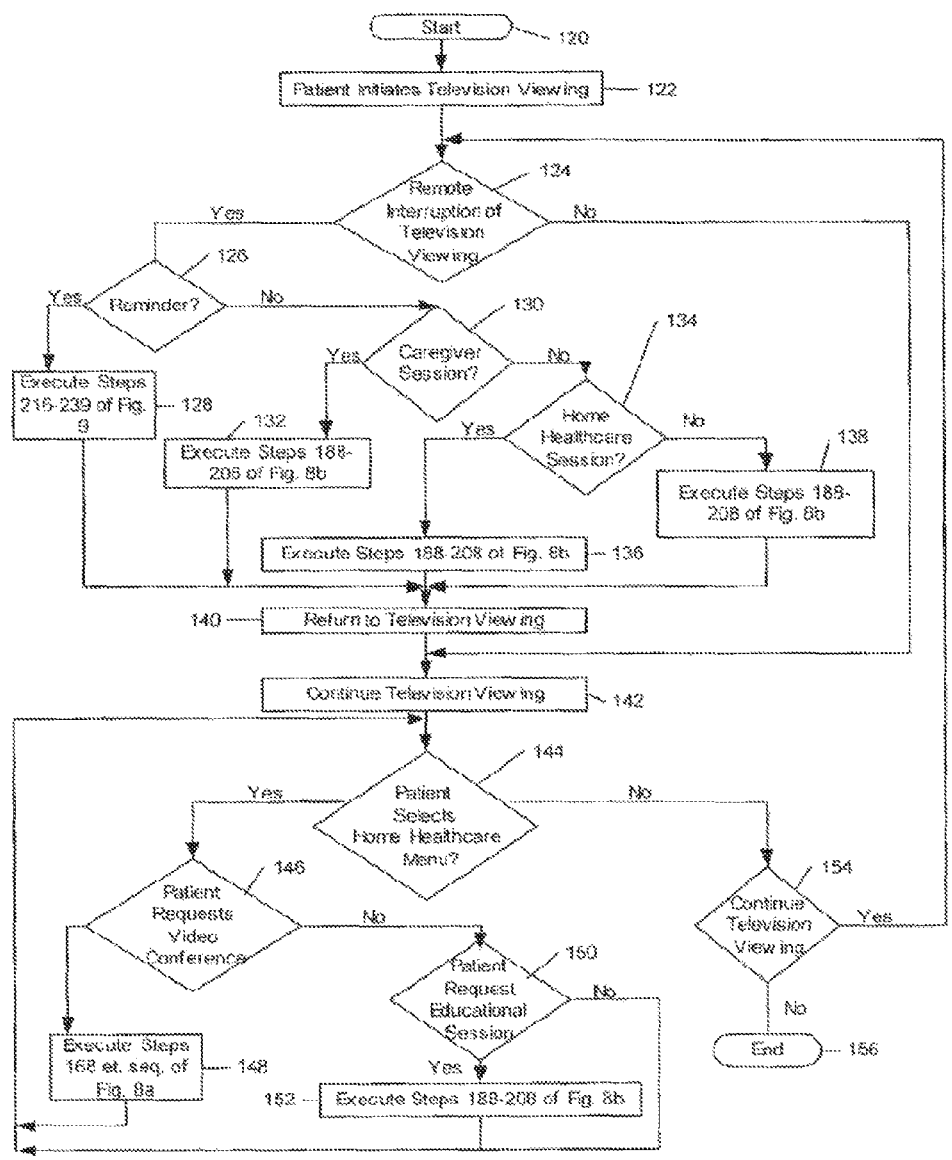
FIG. 7 is a flowchart of a method of patient interaction with the integrated television-based broadband home health system of FIG. 1 via a television set.

Referring next to FIG. 7, a method by which a patient interacts with the integrated television-based broadband home health system of FIG. 1 via a television set will now be described in greater detail. The method commences at step 120 and, at step 122, the patient initiates TV viewing. As previously set forth, TV viewing may be periodically interrupted for previously scheduled events maintained in the event schedule database 90 for the system management station 20. More specifically, the event scheduling application server 80 monitors scheduled events for each patient station 12 forming part of the integrated television-based broadband home health system 10. Upon detection of a scheduled event record maintained in the event schedule database 90 which has a time/date field matching the time/date of the system clock for the event scheduling application server 80, the event scheduling application server 80 retrieves the scheduled event record for execution. Upon retrieval of the scheduled event record from the event schedule database 90, the event scheduling application server 80 constructs a command message for transport to the patient station 12 over the data network 22.

Continuing on to step 124, if a command message originating at the event scheduling application server 80 is received by the home health system interface device 36, the home health system interface device 36 shall interrupt TV viewing by the patient. Accordingly, the method then proceeds to step 126 for determination of the type of interruption to be executed. More specifically, the command message is received by the home health system manager 64 which, in turn, passes the command message to the reminder manager 68. At step 126, the reminder manager 68 examines the command message to determine if TV viewing is to be interrupted to remind the patient of an upcoming event that was previously scheduled. If so, the method proceeds to step 128 where a reminder is issued to the patient by executing steps 216 through 238 of FIG. 9, below. The method then proceeds to step 140 where, upon conclusion of the reminder, TV viewing is resumed.

Returning to step 126, if, however, it is determined that examination of the command message does not indicate that TV viewing is to be interrupted to remind the patient of an upcoming event that was previously scheduled, the method instead proceeds to step 130 where the reminder manager 68 determines, based upon the prior examination of the command message, if the command message indicates that TV viewing is to be interrupted to conduct a remote caregiving session. If so, the method proceeds to step 132 where a remote caregiving session is conducted by executing steps 188 through 208 of FIG. 8b. The method then proceeds to step 140 where, upon conclusion of the remote caregiving session, TV viewing is resumed.

Returning to step 130, if however, it is determined that examination of the command message does not indicate that TV viewing is to be interrupted to conduct a remote caregiving session, the method instead proceeds to step 134 where the reminder manager 68 determines, based upon the prior examination of the command message, if the command message indicates that TV viewing is to be interrupted to conduct a telemedicine or other home healthcare session. If so, the method proceeds to step 136 where a telemedicine or other home healthcare session is conducted by executing steps 188 through 208 of FIG. 8b. The method then proceeds to step 140 where, upon conclusion of the telemedicine or other home healthcare session, TV viewing is resumed.

Figure 8A:
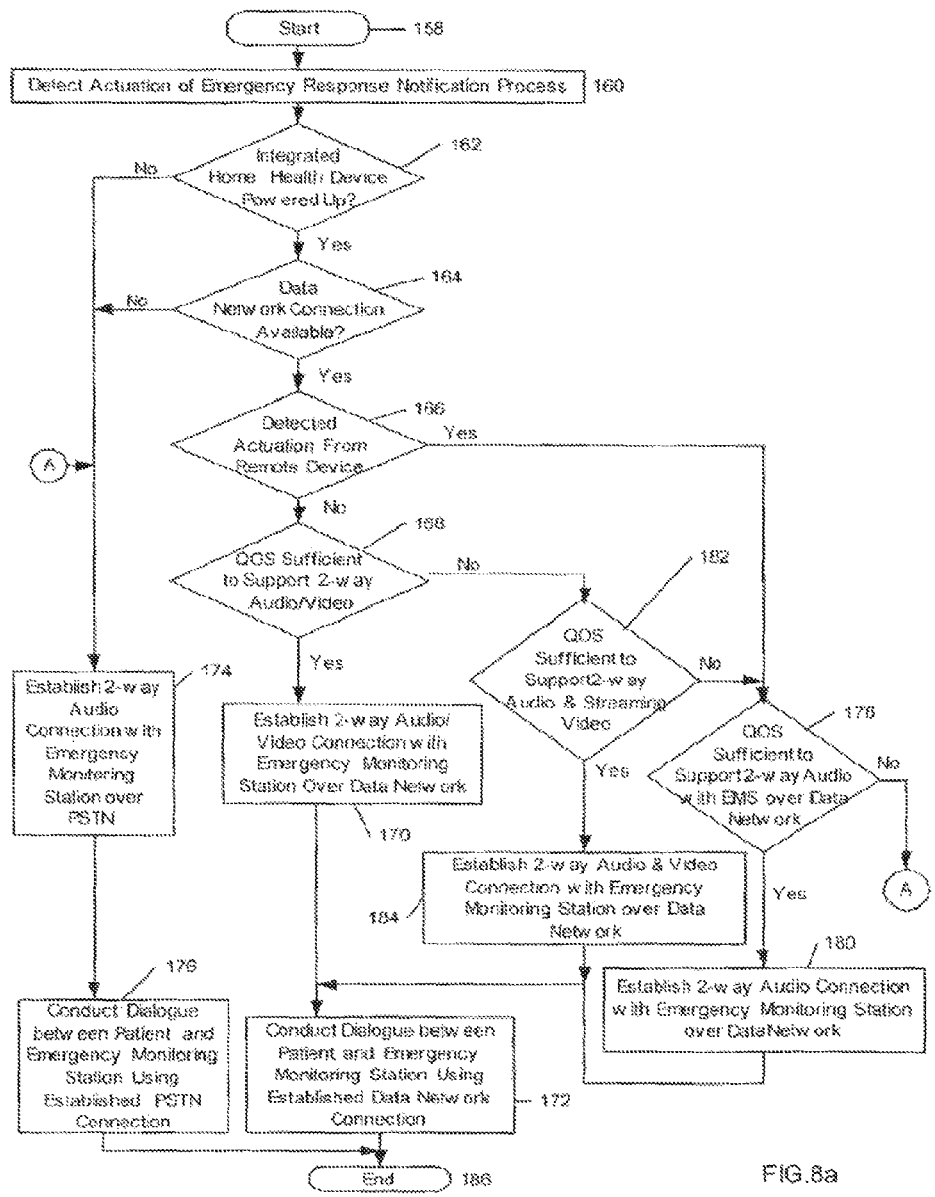
FIG. 8a is a flowchart of a method of responding to a personal emergency using the integrated television-based broadband home health system of FIG. 1.
Figure 8B:
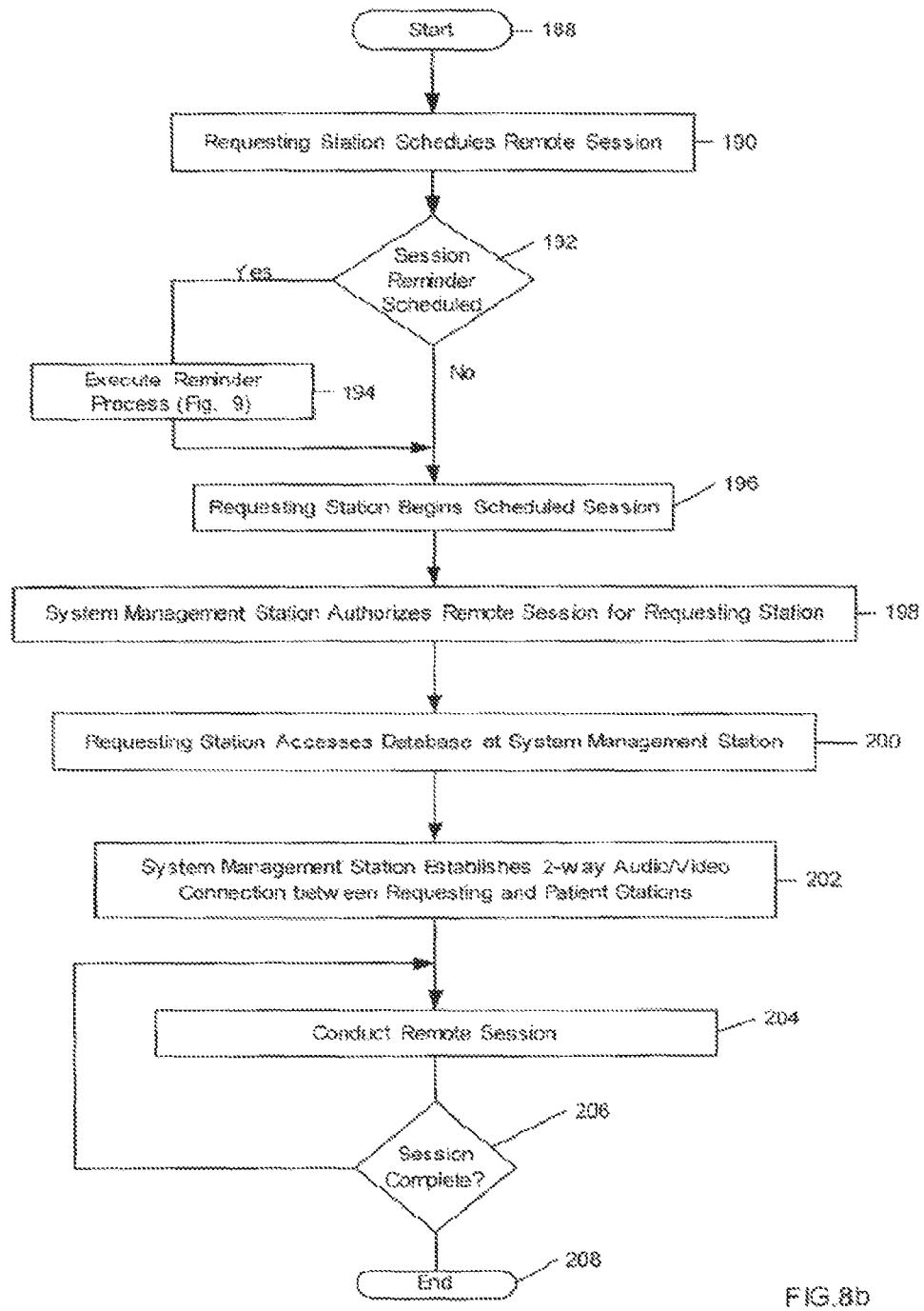
FIG. 8b is a flowchart of a method of conducting a remote session such as a telemedicine, telehealth or remote caregiving session using the integrated television-based broadband home health system of FIG. 1.

Returning to step 134, if, however, it is determined that examination of the command message does not indicate that TV viewing is to be interrupted to conduct a telemedicine or other home healthcare session, the method instead proceeds to step 138 where, having eliminated all other possible scheduled events for which TV viewing may be interrupted, a telehealth or other educational session is conducted by executing steps 188 through 208 of FIG. 8b. The method then proceeds to step 140 wherein, upon conclusion of the telehealth or other education session, TV viewing is resumed.

Proceeding on to step 142, the patient continues TV viewing and, at step 144, the patient may decide to select a home health system menu which may be viewed on the TV 38. To do so, the patient generates an IR control signal to the integrated health system interface device 36 by depressing or otherwise actuating a home health system display button on the patient interface device 52. The IR control signal generated thereby is received by the remote manager 34 which determines, based upon the particular IR control signal received thereby, the appropriate action or actions to take in response thereto. More specifically, in response to receipt of a home health system display command, the remote manager 74 instructs the audio/video manager 72 to interrupt TV viewing in favor of a screening listing one or more operations which the patient may initiate using the patient interface device 52 and, if desired, instructions on how to initiate each of the listed operations.

Proceeding on to step 146, by either depressing or otherwise actuating a "call" button on the patient interface device 32 or by navigating, on the screening to the videoconference selection and then depressing or otherwise actuating an "enter" button on the patient interface device 52, the patient will initiate establishment of a videoconference with monitoring personnel at the emergency response provider station 18. More specifically, by depressing the call button on the patient interface device 52, an IR control signal is generated, again, for receipt by the remote manager 74. Here, however, in response to receipt of a call signal, the remote manager 74 issues a request for videoconference connection to the home health system manager 64. In turn, the home health system manager 64 establishes a two-way video/audio connection with the emergency response provider station 18 over the data network 22. Upon establishment of the two-way video/audio connection, the patient will be able to see and hear monitoring personnel at the emergency response provider station 18 on the TV 38 while the monitoring personnel at the emergency response provider station 18 can see and hear the patient from the video and audio signals respectively generated by the digital imager 40 and the audio receiver 42. Once the two-way video/audio connection is established, the method proceeds to step 148 where a video conference between the patient and the monitoring personnel at the emergency response provider station 18 is conducted by executing steps 168 et seq. of FIG. 8a. The method then returns to step 144 where the patient may select other options form the home healthcare menu.

Returning now to step 144, either depressing or otherwise actuating a "educational video" button on the patient interface device 52 or by navigating, on the screening to the educational video selection and then depressing or otherwise actuating an "enter" button on the patient interface device 52, an IR control signal is generated for receipt by the remote manager 74. The method will then proceed to step 150 where, in response to receipt of the educational video signal, the remote manager 74 will issue an instruction to the audio/video manager 72 to replace the screening currently displayed on the TV 38 with a next screening which lists the various education videos which may be viewed on the TV 38. The patient would then navigate to a desired educational video and again depress or otherwise actuate the enter button on the patient interface device 52. By doing so, the method proceeds to step 152 for viewing of the selected educational video, again, by executing steps 188-208 of FIG. 8b. After completing viewing the selected video at step 152 or, if the patient declined to select a video at step 150, the method returns to step 144 where the patient may continue to select options from the home healthcare menu or may release the menu, thereby proceeding to step 154 where TV viewing is resumed. From step 154, the method will either return to step 124 if the patient continues to view TV or, if the patient has finished viewing TV, the method ends at step 156.

Referring next to FIG. 8a, a method of responding to a personal emergency using the integrated television-based broadband home health system 10 will now be described in greater detail. The method commences at step 158 and, at 160, the emergency response device 54 detects the issuance of an emergency call by the patient located at the patient station 12. Variously, the emergency call may be issued by depressing a wired emergency notification device 57, for example, a panic button, or by depressing a wireless emergency notification device 56, for example, a pendant. By issuing an emergency call, a personal emergency notification process is initiated by the emergency response device 54 issuing a personal emergency notification message to the emergency response device manager 70. The method then proceeds to step 162 where the emergency response device manager 70 determines if the integrated home health system interface device 36 is powered up. If it is determined at step 162 that a power failure has occurred at the integrated home health system interface device 36, the method proceeds to step 174 where the emergency response device manager 70 instructs the emergency response device 54 to establish a two-way audio connection with the emergency response provider station 18 via the PSTN 24. The method would then proceed to step 176 where a dialogue is conducted between the patient located at the patient station 12 and monitoring personnel located at the emergency response provider station 18. Based upon that dialogue, the monitoring personnel located at the emergency response provider station 18 determines whether an emergency situation exists at the patient station 12 and, if so, will dispatch appropriate emergency personnel to address the emergency situation. Having completed an evaluation of the emergency call originated at the patient station, the method ends at step 186.

Returning to step 162, if the emergency response device manager 70 determines that the integrated home health system interface device 36 is powered up, the method instead proceeds to step 164 where the emergency response device manager 70 checks with the home health system manager 64 to see if a data network connection with the emergency response provider station 18 via the data network 22 is available. If the home health system manager 64 advises the emergency response device manager 70 that a data network connection is not available, the method will again proceed through steps 174 and 176 for establishing a two-way audio connection via the PSTN 24, conducting a dialogue between the patient located at the patient station 12 and monitoring personnel located at the emergency response provider station 18 and evaluating the emergency call based upon that dialogue before ending at step 186.

If, however, it is determined by the home health system manager 64 at step 164 that a data network connection over the data network 22 is available, the method proceeds to step 166. At step 166, the home health system manager 64 determines whether the emergency call originated at the wired emergency notification device 57 or the wireless emergency notification device 56. If the emergency call originated at the wired emergency notification device 57, it may be possible for the monitoring personnel at the emergency response provider station 18 to view the patient located at the patient station 12 using the digital imager 40. Accordingly, the method would proceed to step 168. If however, the emergency call originated at the wireless emergency notification device 56, the monitoring personnel at the emergency response provider station 18 would not be able to view the patient located at the patient station 12. Accordingly, the method would instead proceed to step 178.

If, from step 166, the method proceeded to step 168, the home health system manager 64 would, at step 168, check the level of QoS of the data network 22 to determine if the QoS of the data network 22 is sufficient to support a two-way video/audio connection between the patient station 12 and the emergency response provider station 18. If the data network is able to support a two-way video/audio connection between the patient station 12 and the emergency response provider station 18, the method proceeds to step 170 where a two-way video/audio connection between the patient station 12 and the emergency response provider station 18 is established. The method then proceeds to step 172 where the monitoring personnel located at the emergency response provider station 18 conducts a two-way video/audio dialogue with the patient located at the patient station over the data network 22 to evaluate the emergency call. The method would then again end at step 186.

Returning to step 168, if, upon checking the QoS level for the data network 22, the home health system manager 64 determines that the QoS level is insufficient to support a two-way video/audio connection between the patient station 12 and the emergency response station 18 over the data network 22, the method proceeds to step 182 where the home health system manager 64 determines if the QoS of the data network 22 is sufficient to support a two-way audio connection and a one-way streaming video connection between the patient station 12 and the emergency response provider station 18 If the data network 22 can support a two-way audio/one-way streaming video connection between the patient station 12 and the emergency response provider station 18, the method proceeds to step 184 where two-way audio and upstream video connections are established between the patient station 12 and the emergency response provider station 18. The method then continues on to step 172 and proceeds in the manner previously described.

If upon checking the QoS level for the data network 22 and determining, at step 182, that the QoS level for the data network 22 is insufficient to support a two-way audio/one-way Streaming video connection between the patient station 12 and the emergency response station 18 over the data network 22 or upon determining, at step 166, that the emergency call was received from the wireless notification device 56, the method proceeds to step 178 where the health system manager 64 determines if the QoS of the data network 22 is sufficient to support a two-way audio connection between the patient station 12 and the emergency response provider station 18 If the data network 22 can support a two-way audio connection between the patient station 12 and the emergency response provider station 18, the method proceeds to step 180 where a two-way audio connection over the data network 22 is established between the patient station 12 and the emergency response provider station 18. The method then continues on to step 172 and proceeds in the manner previously described.

If, however, the health system manager 64 determines, at step 178, that the QoS of the data network 22 is insufficient to support a two-way audio connection between the patient station 12 and the emergency station 18, the method returns to step 174 for establishment of a two-way audio connection, over the PSTN 24, between the patient station 12 and the emergency response station 18. The method would then proceed in the manner previously described.

Referring next to FIG. 8*b*, a method of conducting a remote session, for example, a telemedicine, telehealth or remote caregiving session with the patient located at the patient station 12, using the integrated television-based broadband home health system 10 will now be described in greater detail. The method starts at step 188 and, at step 190, a requesting station, for example, the healthcare provider station 14 or the caregiver provider station 16 accesses, via the data network 22 and the web server 76, the event scheduling application server 80 to initiate scheduling of a remote session with the patient station 12. While it is contemplated that a remote session is typically scheduled in advance, it is contemplated that a remote session may be scheduled contemporaneously. The requesting station provides the event scheduling application server 80 with information regarding the proposed remote session and, if there are no previously scheduled remote sessions that would conflict with the proposed remote session, the event scheduling application server 80 would schedule the remote session. It is further contemplated that, to avoid the requesting station repeatedly attempting to schedule remote sessions which conflict with previously scheduled sessions, it is contemplated that, when accessing the event scheduling application server 80, a list of previously scheduled events, sortable by patient, date and time of session and duration of session, will be retrieved from the event schedule database 90 and made available for review by the home health provider located at the requesting station.

To schedule a remote event, the requesting station should provide, to the event scheduling application server 80, the type of remote session to be scheduled, the patient station 12 with which the remote session will be conducted, the date and time at which the remote session is to begin, the duration of the remote session, whether any reminders of the remote session should be issued to the patient station, the type of reminders to be issued, the date and time at which the reminders are to be issued, the message to be transmitted to the patient station 12, the duration of the reminder message, whether the message is to be reissued and the frequency at which the reminder message is to be reissued. Using the information provided by the requesting station, the event scheduling application server 80 constructs an appropriate number of scheduled event entries in the event schedule database 90. Typically, a first entry is constructed for the remote session itself and an additional entry is constructed for each remote session reminder to be issued.

After scheduling a remote session, the method proceeds to step 192. At step 192, the event scheduling application server 80 periodically checks the contents of the event schedule database 90 for events requiring execution. Thus, if a reminder (or reminders) of the session were scheduled at step 190, the event scheduling application server 80 will determine that the reminder (or reminders) require execution when the date and time at which they were scheduled for execution matches the current date and time for the event scheduling application server 80. The method then proceeds to step 194 for execution, for each reminder scheduled, of the reminder process set forth in FIG. 9 and described in greater detail below. After execution of the reminder process of FIG. 9 for each reminder scheduled or, if no reminders were scheduled, the method then proceeds to step 196 for initiation of a scheduled remote session.

Proceeding on to step 196, the requesting station initiates a scheduled session by accessing, via the data network 22 and the web server 76, the video conference application server 82. Upon accessing the video conference application server 82, the requesting station provides the video conference application server 82 with identifying information, for example, a user name and password. The method then proceeds onto step 198 where the video conference application server 82 checks the provided identifying information against identifying information for a series of authorized stations and/or users maintained in the video conferencing authorization database 94. If a check of the video conferencing authorization database 92 indicates that the requesting station is authorized to conduct a session with the patient station 12, the method proceeds to step 200 where, in preparation for the remote session, the requesting station would access, via the data network 22 and the web server 76, the EPR management application server 84. By accessing the EPR management application server 84, the requesting station may retrieve, from the electronic patient records database 84, the electronic patient record for the patient located at the patient station 12.

Proceeding on to step 202, the video conference application server 82 establishes a two-way video and audio connection between the requesting station and the patient station and, at step 204, the remote session is conducted. During the remote session, the home health provider located at the requesting station may perform a variety of services for the patient location at the patient station 12 including, but not necessarily limited to, reviewing the current electronic patient record for the patient, conducting a dialogue with the patient, visually observing the mannerisms of the patient, visually examining the patient's body, acquiring real-time medical data for the patient and updating the electronic patient record for the patient. The session will continue until terminated at step 206. It is contemplated that a variety of techniques may be used to terminate a session. Typically, the session will continue until the requesting station terminates the two-way video/audio connection with the patient station 12. If the session is time limited, however, it is contemplated that, after issuance of one or more warnings to the requesting station and/or the patient station 12, the two-way video/audio connection may be terminated by the video conference application server 82.

Figure 9:
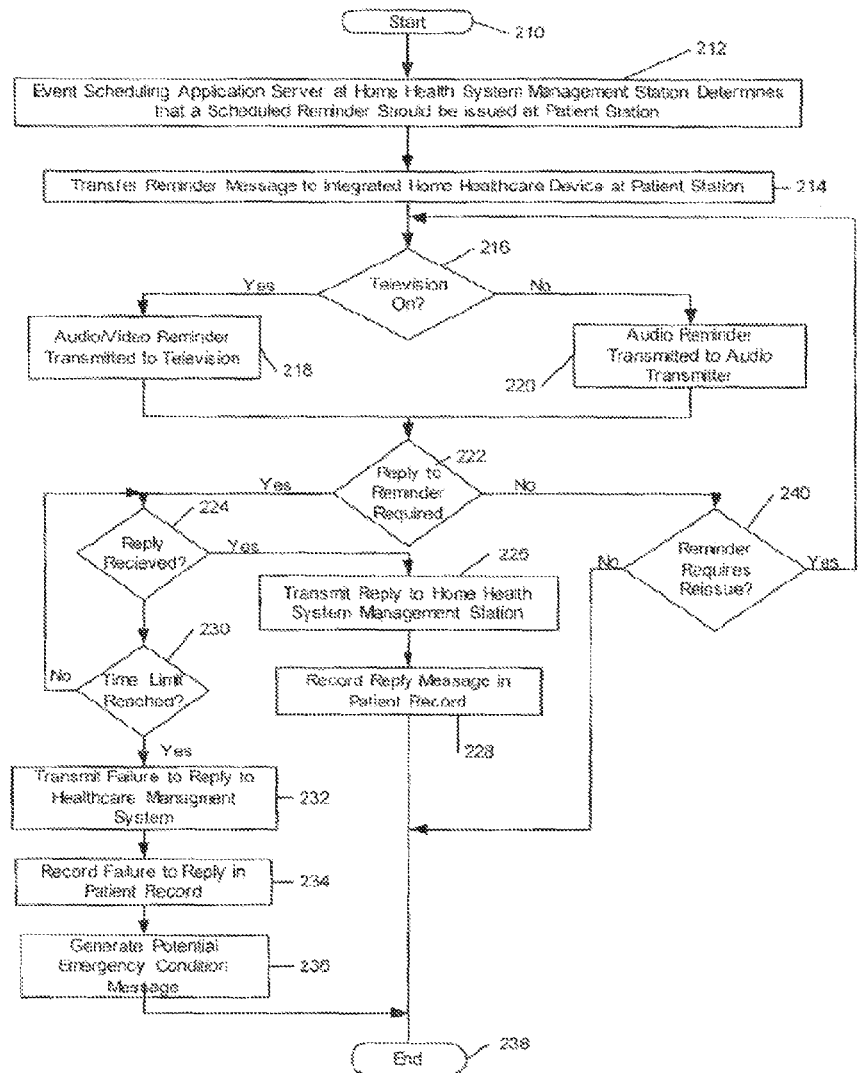
FIG. 9 is a flowchart of a method of issuing reminders to patients using the integrated television-based broadband home health system of FIG. 1.

Referring next to FIG. 9, a method of issuing reminders to patients located at patient stations, for example, the patient station 12, using the integrated television-based broadband home health system 10 will now be described in greater detail. The method starts at step 210 and, at step 212, the event scheduling application server 80 determines that a scheduled reminder should be issued at the patient station 12. To do so, the event scheduling application server 80 periodically checks the contents of the event schedule database 90 for events requiring execution and, if a reminder event stored in the event schedule database 90 is scheduled for execution at a date and time matching the current date and time for the event scheduling application server 80, the event scheduling application server 80 determines that the scheduled reminder is to be executed.

Proceeding on to step 214, the reminder event stored in the event schedule database 90 is retrieved and a data packet is constructed for transmission to the patient station 12 indicated as the destination of the reminder message. The constructed data packet should contain data from which the audible and/or visible reminder message to be broadcast at the patient station 12 may be constructed, the type of reminder message to be broadcast at the patient station 12, the duration of the reminder message, whether the reminder message is to be reissued and the frequency at which the reminder message is to be reissued. Once constructed, the data packet is transmitted, over the data network 22, to the patient station 12. The home health system manager 64 passes the arriving data packet to the reminder manager 68 where the data packet is checked for type of reminder message to be broadcast and, if the reminder message is the type of message requiring a response within a first pre-selected period of time, the reminder manager 68 would begin a countdown of the first pre-selected time period and then pass the data from which the audible and/or visible reminder message to be broadcast may be constructed to the audio/video manager 72 where the audible and/or visible reminder message is constructed from the received data. Conversely, if the reminder message is the type of message requiring one or more reissues thereof after a second pre-selected period of time, the reminder manager 68 would begin a countdown of the second pre-selected period of time and then pass the data from which the audible and/or visible reminder message to be broadcast may be constructed to the audio/video manager 72 where, as before, the audible and/or visible reminder message is constructed from the received data.

Proceeding on to step 216, the audio/video manager 72 checks to see if the TV 38 is turned on. If the TV 38 is on, the method proceeds to step 218 where the audio/video manager 72 transmits the audible and/or visible reminder message to the TV 38 for the visual and/or audible broadcast thereof. If, however, the audio/video manager 72 determines that the TV 38 is turned off, the method will instead proceed to step 220 where the audio/video manager 72 transmits an audible portion of the audible and/or visible reminder message to the audio transmitter 44 for the audible broadcast thereof. From either step 218 or step 220, the method then proceeds to step 222. If, at step 222, the reminder manager 68 indicates that no reply to the reminder message is required, the method proceeds to step 240 for determining if the reminder message requires reissue. If the reminder manager 68 determines that the reminder message does not have to be reissued, the method ends at step 238. If, however, the reminder manager 68 determines that the reminder message is to be reissued and that the second pre-determined period of time has elapsed, the method returns to step 216 where the audio/video manager 72 resets the countdown of the second pre-determined period of time and timer and retransmits the reminder message to the audio/video manager 72 for the rebroadcast thereof. The method then repeats until the reminder message no longer requires reissue. Generally, the reminder manager 68 maintains a reminder reissue count and ends retransmission of the reminder message when the reminder re-issue count reaches zero.

Returning now to step 222, if a reply to the reminder message is required, the method proceeds to step 224 for determination as to whether the reminder manager 68 has received a reply, in the form, of a reply message received from the remote manager 74, to the reminder message. If the reply has been received, the method proceeds to step 226 where the reply message received by the reminder manager 68 is forwarded to the EPR management application server 84 at the system management station 20 where the record for the patient located at the patient station 12 stored in the electronic patient records database 94 is updated to include an indication of the reply to the reminder message. The method then ends at step 238.

Returning to step 222, if the reminder manager 68 has not yet received a reply from the remote manager 74, the method proceeds to step 230 to await expiration of the first pre-selected period of time. The method cycles through step 224 and step 230 until either the reply message is received from the remote manager or the first pre-selected period of time expires. If, at step 230, the first pre-selected period of time expires without receipt of a reply message, the method proceeds to step 232 where the reminder manager 68 constructs a failure message indicating that no reply to the reminder message was ever received. The failure message is transferred to the forwarded to the EPR management application server 84 at the system management station 20 where, at step 234, the record for the patient located at the patient station 12 stored in the electronic patient records database 94 is updated to include an indication of the failure to reply to the reminder message. The method then proceeds to step 236 where the reminder manager 68 constructs a potential emergency condition message indicating that a potential emergency condition may be present at the patient station. The potential emergency message is then forwarded to the emergency response provider station 18 where, upon receipt of the potential emergency message, the monitoring personnel located at the emergency response station 18 will investigate further in the manner previously described to determine if an emergency condition exists at the patient station 12. The method then ends at step 238.

Thus, there has been described and illustrated herein, a home health system which integrates one or more of personal emergency response, life safety, telemedicine, telehealth, and remote caregiving services into a single, television-based, broadband, networked, home health system. However, those skilled in the art should recognize that numerous modifications and variations may be made in the techniques disclosed herein without departing substantially from the spirit and scope of the invention. Accordingly, the scope of the invention should only be defined by the claims appended hereto.

What is claimed is:

1. A communication system comprising:
a first interface configured to receive first content from a first service provider via radio frequency;
a second interface configured to receive second content from a second service provider via a broadband data network; and
a third interface configured to transmit the first content to a user device, to transmit the second content to the user device based upon a determination to interrupt the first content, and to transmit at least the second content to the user device independent of a request from the user device,
wherein one or more of the first interface, the second interface, and the third interface, facilitates two-way communication between the user device and one or more of the first service provider and the second service provider.

2. The communication system of claim 1, wherein the first content comprises a television signal.

3. The communication system of claim 1, wherein the second content comprises one or more of an alert, a command message, a notification, and a reminder.

4. The communication system of claim 1, wherein the third interface is further configured to selectively and simultaneously transmit the first content and the second content to the user device.

5. The communication system of claim 1, wherein one or more of the first service provider and the second service provider is a home health services provider.

6. The communication system of claim 1, wherein one or more of the first service provider and the second service provider is a television service provider.

7. The communication system of claim 1, wherein the third interface is selectively operable to transmit one or more of video signals and audio signals to the user device.

8. The communication system of claim 1, further comprising a system management station coupled to the broadband data network, the system management station remotely located relative to the user device, wherein the system management station is configured to authorize one or more of the first service provider and the second service provider to communicate with the user device.

9. The communication system of claim 1, wherein the determination to interrupt the first content is based upon one or more of a predefined schedule, a type of content included in the second content, or an urgency of the second content.

10. A communication system comprising:
a first interface configured to receive first content from a first service provider via radio frequency;
a second interface configured to receive second content from a second service provider via a broadband data network; and
a user device in communication with the first interface and the second interface, the user device configured to receive the second content upon determining to interrupt the first content, and to receive at least the second content independent of a request from the user device,
wherein one or more of the first interface and the second interface facilitates two-way communication between the user device and one or more of the first service provider and the second service provider.

11. The communication system of claim 10, wherein the user device is further configured to render one or more of the first content and the second content.

12. The communication system of claim 10, wherein the user device is further configured to overlay one or more of the first content and the second content.

13. The communication system of claim 10, wherein the first content comprises a television signal.

14. The communication system of claim 10, wherein the second content comprises one or more of an alert, a notification, and a reminder.

15. The communication system of claim 10, wherein the user device is further configured to selectively and simultaneously render the first content and the second content.

16. The communication system of claim 10, wherein one or more of the first service provider and the second service provider is a home health services provider.

17. The communication system of claim 10, wherein one or more of the first service provider and the second service provider is a television service provider.

18. The communication system of claim 10, further comprising a system management station coupled to the broadband data network, the system management station remotely located relative to the user device, wherein the system management station is configured to authorize one or more of the first service provider and the second service provider to communicate with the user device.

19. The communication system of claim 10, wherein the determination to interrupt the first content is based upon one or more of a predefined schedule, a type of content included in the second content, or an urgency of the second content.

20. A communication system comprising:
an interface device comprising a first communication path configured to receive first content from a first service provider via radio frequency and a second communication path configured to receive second content from a second service provider via a broadband data network; and
a user device in communication the interface device,
wherein the interface device is further configured to transmit the first content to the user device and to transmit the second content to the user device based upon a determination to interrupt the first content independent of a request from the user device for transmission of the second content, and
wherein the interface device facilitates two-way communication between the user device and one or more of the first service provider and the second service provider.

21. The communication system of claim 20, wherein the user device is further configured to render one or more of the first content and the second content.

22. The communication system of claim 20, wherein the user device is further configured to overlay one or more of the first content and the second content.

23. The communication system of claim 20, wherein the first content comprises a television signal.

24. The communication system of claim 20, wherein the second content comprises one or more of an alert, a notification, and a reminder.

25. The communication system of claim 20, wherein the interface device is further configured to selectively simultaneously transmit the first content and the second content to the user device.

26. The communication system of claim 20, wherein one or more of the first service provider and the second service provider is a home health services provider.

27. The communication system of claim 20, wherein one or more of the first service provider and the second service provider is a television service provider.

28. The communication system of claim 20, wherein the interface device is selectively operable to transmit one or more of video signals and audio signals to the user device.

29. The communication system of claim 20, further comprising a system management station coupled to the broadband data network, the system management station remotely located relative to the user device, wherein the system management station is configured to authorize one or more of the first service provider and the second service provider to communicate with the user device.

30. The communication system of claim 20, further comprising a medical device coupled to the interface device, wherein the interface device is configured to transmit data signals received from the medical device to one or more of the first service provider and the second service provider.

31. The communication system of claim 20, wherein the interface device is further configured to determine the appropriate path of the first communication path and the second communication path for establishing connection between the user device and one or more of the first service provider and the second service provider by further determining:
whether the broadband data network is available; and
whether the broadband data network has a quality of service (QoS) level sufficient to support two-way video/audio connection.

32. The communication system of claim 20, further comprising an audio receiver coupled to the interface device and a digital imager coupled to the interface device, wherein the interface device is configured to transmit audio and video signals received from one or more of the audio receiver and the digital imager to one or more of the first service provider and the second service provider.

33. The communication system of claim 20, wherein the determination to interrupt the first content is based upon one or more of a predefined schedule, a type of content included in the second content, or an urgency of the second content.

* * * * *